(12) United States Patent
Nozawa et al.

(10) Patent No.: US 8,034,574 B2
(45) Date of Patent: Oct. 11, 2011

(54) SCREENING METHOD FOR PROKINETIC AGENT

(75) Inventors: Katsura Nozawa, Chuo-ku (JP); Eri Shoda, Chuo-ku (JP); Hitoshi Doihara, Chuo-ku (JP); Ryosuke Kojima, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 190 days.

(21) Appl. No.: 12/302,808

(22) PCT Filed: Oct. 5, 2007

(86) PCT No.: PCT/JP2007/069622
§ 371 (c)(1),
(2), (4) Date: Nov. 28, 2008

(87) PCT Pub. No.: WO2008/044660
PCT Pub. Date: Apr. 17, 2008

(65) Prior Publication Data
US 2010/0129345 A1 May 27, 2010

(30) Foreign Application Priority Data
Oct. 6, 2006 (JP) .................................. 2006 275837

(51) Int. Cl.
*G01N 33/53* (2006.01)
*G01N 33/566* (2006.01)
*C12Q 1/68* (2006.01)
(52) U.S. Cl. ............... 435/7.2; 435/7.1; 435/6; 436/501
(58) Field of Classification Search .................. None
See application file for complete search history.

(56) References Cited

FOREIGN PATENT DOCUMENTS
| | | |
|---|---|---|
| JP | 2006-199647 | 8/2006 |
| WO | WO 2005/089206 A2 | 9/2005 |
| WO | WO 2005089206 A2 * | 9/2005 |
| WO | WO 2007/073505 A2 | 6/2007 |
| WO | WO 2007/073505 A3 | 6/2007 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Bandell et al. (2004). Noxious cold ion channel TRPA1 is activated by pungent compounds and bradykinin. Neuron. 41:849-857.*
Alexander Stokes, et al., "TRPA1 is a Substrate for de-ubiquitination by the Tumor Suppressor CYLD", Cellular Signalling, vol. 18, No. Oct. 10, 2006, pp. 1584-1594.
Hiroshi Watanabe, et al., "Central Effects of Cinnamaldehyde", Journal of the Pharmaceutical Society of Japan, vol. 104, No. 10, 1984, pp. 1095-1100.
Diana M. Bautista, et al., "TRPA1 Mediates the Inflammatory Actions of Environmental Irritants and Proalgesic Agents", Cell, vol. 124, No. 6, Mar. 24, 2006, pp. 1269-1282.
Peter Holzer, "Gastrointestinal Pain in Functional Bowel Disorders: Sensory Neurons as Novel Drug Targets", Expert Opinion on Therapeutic Targets, vol. 8, No. 2, Apr. 2004, pp. 107-123 with cover page.
Sven-Eric Jordt, et al., "Mustard Oils and Cannabinoids excite sensory nerve fibres through the TRP Channel ANKTM1", Nature, Letters to Nature, vol. 427, Jan. 15, 2004, pp. 260-265.
Gina M. Story, et al., "ANKTM1, a TRP-like Channel Expressed in Nociceptive Neurons, is Activated by Cold Temperatures", Cell, vol. 112, Mar. 21, 2003, pp. 819-829.
William L. Hasler, et al., "Irritable Bowel Syndrome Pathophysiology" Textbook of Gastroenterology, 4th Edition, Chapter 86, ISBN 0-7817-2861-4, 7 pages.
Diana M. Bautista, et al., "Pungent products from garlic activate the sensory ion channel TRPA1", Proceedings of the National Academy of Sciences of USA, vol. 102, No. 34, XP009125805, Aug. 23, 2005, pp. 12248-12252.
Barbara Namer, et al., "TRPA1 and TRPM8 activation in humans: effects of cinnamaldehyde and menthol", NeuroReport, vol. 16, No. 9, XP 009091531, Jun. 21, 2005, pp. 955-959.
Aerssens Jeroen, et al., "Altered expression of TRP, Ca2+ and K+ channels in vagal visceral afferents in a post-infectious model of irritable bowel syndrome (IBS)", Biosis, XP-002433340, Apr. 1, 2006, 1 page.
Lin Jiahui, et al., "Properties of Human TRPa1, a Mechanosensitive Channel and Putative Nociceptor" AGA Abstracts, Gastroenterology, vol. 130, No. 4, Suppl. 2, XP 009086552, Apr. 2006, p. A225.
Peter Holzer, et al. "Stimulation of the Brain-Gut Axis by Intracolonic Mustard Oil is Enhanced in Mice with low-Grade Colitis", AGA Abstracts, Gastroenterology, vol. 132, No. 4, Suppl. 2, XP009125772, Apr. 2007, p. A720.
Angelica Penuelas, et al., "Contractile effect of TRPA1 receptor agonists in the isolated mouse intestine", European Journal of Pharmacology, vol. 576, No. 1-3, XP0022307550, Dec. 8, 2007, pp. 143-150. S. Hayashi, et al., "Impairment by activation of TRPA1 of gastric epithelial restitution in a wound model using RGM1 cell monolayer", Inflammopharmacology, vol. 15, No. 3, XP009125779, Oct. 1, 2007, pp. 218-222.
João B. Calixto, et al., "Contribution of natural products to the discovery of the transient receptor potential (TRP) channels family and their functions", Pharmacology and Therapeutics, vol. 106, No. 2, XP004870342, May 1, 2005, pp. 179-208.
Katsura Nozawa, et al., "TRPA1 regulates gastrointestinal motility through serotonin release from enterochromaffin cells", Proceedings of the National Academy of Sciences of the United States of America, vol. 106, No. 9, XP002555859, pp. 3408-3413, 2009.
Keiichi Nagata et al., "Nociceptor and Hair Cell Transducer Properties of TRPA1, a Channel for Pain and Hearing", The Journal of Neuroscience, Apr. 20, 2005, vol. 25 (16), pp. 4052-4061.

* cited by examiner

*Primary Examiner* — Christine J Saoud
*Assistant Examiner* — Jon M Lockard
(74) *Attorney, Agent, or Firm* — Oblon, Spivak, McClelland, Maier & Neustadt, L.L.P.

(57) ABSTRACT

The present invention provides a screening tool and screening method for obtaining a substance useful as a prophylactic and/or therapeutic drug for diseases associated with 5-HT production/secretion abnormalities, including digestive organ diseases, and a prophylactic and/or therapeutic drug for diseases associated with 5-HT production/secretion abnormalities, including digestive organ diseases. Examples of digestive organ diseases in the present invention include constipation type irritable bowel syndrome, functional dyspepsia, constipation, diarrhea type irritable bowel syndrome, diarrhea and vomiting.

12 Claims, 8 Drawing Sheets

(A)

(B)

(C)

antisense probe　　　　　sense probe

SEQUENCE LISTING

```
<160> NUMBER OF SEQ ID NOS: 16

<210> SEQ ID NO 1
<211> LENGTH: 3360
<212> TYPE: DNA
<213> ORGANISM: Homo sapiens
<220> FEATURE:
<221> NAME/KEY: CDS
<222> LOCATION: (1)..(3360)

<400> SEQUENCE: 1 atg aag tgc agc ctg agg aag atg tgg cgc cct gga gaa aag aag gag      48
Met Lys Cys Ser Leu Arg Lys Met Trp Arg Pro Gly Glu Lys Lys Glu
1               5                   10                  15 ccc cag ggc gtt gtc tat gag gat gtg ccg gac gac acg gag gat ttc      96
Pro Gln Gly Val Val Tyr Glu Asp Val Pro Asp Asp Thr Glu Asp Phe
            20                  25                  30 aag gaa tcg ctt aag gtg gtt ttt gaa gga agt gca tat gga tta caa     144
Lys Glu Ser Leu Lys Val Val Phe Glu Gly Ser Ala Tyr Gly Leu Gln
        35                  40                  45 aac ttt aat aag caa aag aaa tta aaa aca tgt gac gat atg gac acc     192
Asn Phe Asn Lys Gln Lys Lys Leu Lys Thr Cys Asp Asp Met Asp Thr
```

-continued

```
             50                  55                  60
ttc ttg cat tat gct gca gca gaa ggc caa att gag cta atg gag       240
Phe Phe Leu His Tyr Ala Ala Ala Glu Gly Gln Ile Glu Leu Met Glu
 65                  70                  75                  80 aag atc acc aga gat tcc tct ttg gaa gtg ctg cat gaa atg gat gat   288
Lys Ile Thr Arg Asp Ser Ser Leu Glu Val Leu His Glu Met Asp Asp
                     85                  90                  95 tat gga aat acc cct ctg cat tgt gct gta gaa aaa aac caa att gaa   336
Tyr Gly Asn Thr Pro Leu His Cys Ala Val Glu Lys Asn Gln Ile Glu
                100                 105                 110 agc gtt aag ttt ctt ctc agc aga gga gca aac cca aac ctc cga aac   384
Ser Val Lys Phe Leu Leu Ser Arg Gly Ala Asn Pro Asn Leu Arg Asn
            115                 120                 125 ttc aac atg atg gct cct ctc cac ata gct gtg cag ggc atg aat aat   432
Phe Asn Met Met Ala Pro Leu His Ile Ala Val Gln Gly Met Asn Asn
        130                 135                 140 gag gtg atg aag gtc ttg ctt gag cat aga act att gat gtt aat ttg   480
Glu Val Met Lys Val Leu Leu Glu His Arg Thr Ile Asp Val Asn Leu
145                 150                 155                 160 gaa gga gaa aat gga aac aca gct gtg atc att gcg tgc acc aca aat   528
Glu Gly Glu Asn Gly Asn Thr Ala Val Ile Ile Ala Cys Thr Thr Asn
                165                 170                 175 aat agc gaa gca ttg cag att ttg ctt aac aaa gga gct aag cca tgt   576
Asn Ser Glu Ala Leu Gln Ile Leu Leu Asn Lys Gly Ala Lys Pro Cys
            180                 185                 190 aaa tca aat aaa tgg gga tgt ttc cct att cac caa gct gca ttt tca   624
Lys Ser Asn Lys Trp Gly Cys Phe Pro Ile His Gln Ala Ala Phe Ser
        195                 200                 205 ggt tcc aaa gaa tgc atg gaa ata ata cta agg ttt ggt gaa gag cat   672
Gly Ser Lys Glu Cys Met Glu Ile Ile Leu Arg Phe Gly Glu Glu His
210                 215                 220 ggg tac agt aga cag ttg cac att aac ttt atg aat aat ggg aaa gcc   720
Gly Tyr Ser Arg Gln Leu His Ile Asn Phe Met Asn Asn Gly Lys Ala
225                 230                 235                 240 acc cct ctc cac ctg gct gtg caa aat ggt gac ttg gaa atg atc aaa   768
Thr Pro Leu His Leu Ala Val Gln Asn Gly Asp Leu Glu Met Ile Lys
                245                 250                 255 atg tgc ctg gac aat ggt gca caa ata gac cca gtg gag aag gga agg   816
Met Cys Leu Asp Asn Gly Ala Gln Ile Asp Pro Val Glu Lys Gly Arg
            260                 265                 270 tgc aca gcc att cat ttt gct gcc acc cag gga gcc act gag att gtt   864
Cys Thr Ala Ile His Phe Ala Ala Thr Gln Gly Ala Thr Glu Ile Val
        275                 280                 285 aaa ctg atg ata tcg tcc tat tct ggt agc gtg gat att gtt aac aca   912
Lys Leu Met Ile Ser Ser Tyr Ser Gly Ser Val Asp Ile Val Asn Thr
290                 295                 300 acc gat gga tgt cat gag acc atg ctt cac aga gct tca ttg ttt gat   960
Thr Asp Gly Cys His Glu Thr Met Leu His Arg Ala Ser Leu Phe Asp
305                 310                 315                 320 cac cat gag cta gca gac tat tta att tca gtg gga gca gat att aat   1008
His His Glu Leu Ala Asp Tyr Leu Ile Ser Val Gly Ala Asp Ile Asn
                325                 330                 335 aag atc gat tct gaa gga cgc tct cca ctt ata tta gca act gct tct   1056
Lys Ile Asp Ser Glu Gly Arg Ser Pro Leu Ile Leu Ala Thr Ala Ser
            340                 345                 350 gca tct tgg aat att gta aat ttg cta ctc tct aaa ggt gcc caa gta   1104
Ala Ser Trp Asn Ile Val Asn Leu Leu Leu Ser Lys Gly Ala Gln Val
        355                 360                 365 gac ata aaa gat aat ttt gga cgt aat ttt ctg cat tta act gta cag   1152
Asp Ile Lys Asp Asn Phe Gly Arg Asn Phe Leu His Leu Thr Val Gln
```

```
             370                 375                 380
caa cct tat gga tta aaa aat ctg cga cct gaa ttt atg cag atg caa    1200
Gln Pro Tyr Gly Leu Lys Asn Leu Arg Pro Glu Phe Met Gln Met Gln
385                 390                 395                 400 cag atc aaa gag ctg gta atg gat gaa gac aac gat ggg tgt act cct    1248
Gln Ile Lys Glu Leu Val Met Asp Glu Asp Asn Asp Gly Cys Thr Pro
                405                 410                 415 cta cat tat gca tgt aga cag ggg ggc cct ggt tct gta aat aac cta    1296
Leu His Tyr Ala Cys Arg Gln Gly Gly Pro Gly Ser Val Asn Asn Leu
            420                 425                 430 ctt ggc ttt aat gtg tcc att cat tcc aaa agc aaa gat aag aaa tca    1344
Leu Gly Phe Asn Val Ser Ile His Ser Lys Ser Lys Asp Lys Lys Ser
        435                 440                 445 cct ctg cat ttt gca gcc agt tat ggg cgt atc aat acc tgt cag agg    1392
Pro Leu His Phe Ala Ala Ser Tyr Gly Arg Ile Asn Thr Cys Gln Arg
    450                 455                 460 ctc cta caa gac ata agt gat acg agg ctt ctg aat gaa ggt gac ctt    1440
Leu Leu Gln Asp Ile Ser Asp Thr Arg Leu Leu Asn Glu Gly Asp Leu
465                 470                 475                 480 cat gga atg act cct ctc cat ctg gca gca aag aat gga cat gat aaa    1488
His Gly Met Thr Pro Leu His Leu Ala Ala Lys Asn Gly His Asp Lys
                485                 490                 495 gta gtt cag ctt ctt ctg aaa aaa ggt gca ttg ttt ctc agt gac cac    1536
Val Val Gln Leu Leu Leu Lys Lys Gly Ala Leu Phe Leu Ser Asp His
            500                 505                 510 aat ggc tgg aca gct ttg cat cat gcg tcc atg ggc ggg tac act cag    1584
Asn Gly Trp Thr Ala Leu His His Ala Ser Met Gly Gly Tyr Thr Gln
        515                 520                 525 acc atg aag gtc att ctt gat act aat ttg aag tgc aca gat cgc ttg    1632
Thr Met Lys Val Ile Leu Asp Thr Asn Leu Lys Cys Thr Asp Arg Leu
    530                 535                 540 gat gaa gac ggg aac act gca ctt cac ttt gct gca agg gaa ggc cac    1680
Asp Glu Asp Gly Asn Thr Ala Leu His Phe Ala Ala Arg Glu Gly His
545                 550                 555                 560 gcc aaa gcc gtt gcg ctt ctc ctg agc cac aat gct gac ata gtc ctg    1728
Ala Lys Ala Val Ala Leu Leu Leu Ser His Asn Ala Asp Ile Val Leu
                565                 570                 575 aac aag cag cag gcc tcc ttt ttg cac ctt gca ctt cac aat aag agg    1776
Asn Lys Gln Gln Ala Ser Phe Leu His Leu Ala Leu His Asn Lys Arg
            580                 585                 590 aag gag gtt gtt ctt acg atc atc agg agc aaa aga tgg gat gaa tgt    1824
Lys Glu Val Val Leu Thr Ile Ile Arg Ser Lys Arg Trp Asp Glu Cys
        595                 600                 605 ctt aag att ttc agt cat aat tct cca ggc aat aaa tgt cca att aca    1872
Leu Lys Ile Phe Ser His Asn Ser Pro Gly Asn Lys Cys Pro Ile Thr
    610                 615                 620 gaa atg ata gaa tac ctc cct gaa tgc atg aag gta ctt tta gat ttc    1920
Glu Met Ile Glu Tyr Leu Pro Glu Cys Met Lys Val Leu Leu Asp Phe
625                 630                 635                 640 tgc atg ttg cat tcc aca gaa gac aag tcc tgc cga gac tat tat atc    1968
Cys Met Leu His Ser Thr Glu Asp Lys Ser Cys Arg Asp Tyr Tyr Ile
                645                 650                 655 gag tat aat ttc aaa tat ctt caa tgt cca tta gaa ttc acc aaa aaa    2016
Glu Tyr Asn Phe Lys Tyr Leu Gln Cys Pro Leu Glu Phe Thr Lys Lys
            660                 665                 670 aca cct aca cag gat gtt ata tat gaa ccg ctt aca gcc ctc aac gca    2064
Thr Pro Thr Gln Asp Val Ile Tyr Glu Pro Leu Thr Ala Leu Asn Ala
        675                 680                 685 atg gta caa aat aac cgc ata gag ctt ctc aat cat cct gtg tgt aaa    2112
Met Val Gln Asn Asn Arg Ile Glu Leu Leu Asn His Pro Val Cys Lys
```

```
                 690                 695                 700
gaa tat tta ctc atg aaa tgg ttg gct tat gga ttt aga gct cat atg    2160
Glu Tyr Leu Leu Met Lys Trp Leu Ala Tyr Gly Phe Arg Ala His Met
705                 710                 715                 720 atg aat tta gga tct tac tgt ctt ggt ctc ata cct atg acc att ctc    2208
Met Asn Leu Gly Ser Tyr Cys Leu Gly Leu Ile Pro Met Thr Ile Leu
                725                 730                 735 gtt gtc aat ata aaa cca gga atg gct ttc aac tca act ggc atc atc    2256
Val Val Asn Ile Lys Pro Gly Met Ala Phe Asn Ser Thr Gly Ile Ile
            740                 745                 750 aat gaa act agt gat cat tca gaa ata cta gat acc acg aat tca tat    2304
Asn Glu Thr Ser Asp His Ser Glu Ile Leu Asp Thr Thr Asn Ser Tyr
        755                 760                 765 cta ata aaa act tgt atg att tta gtg ttt tta tca agt ata ttt ggg    2352
Leu Ile Lys Thr Cys Met Ile Leu Val Phe Leu Ser Ser Ile Phe Gly
    770                 775                 780 tat tgc aaa gaa gcg ggg caa att ttc caa cag aaa agg aat tat ttt    2400
Tyr Cys Lys Glu Ala Gly Gln Ile Phe Gln Gln Lys Arg Asn Tyr Phe
785                 790                 795                 800 atg gat ata agc aat gtt ctt gaa tgg att atc tac acg acg ggc atc    2448
Met Asp Ile Ser Asn Val Leu Glu Trp Ile Ile Tyr Thr Thr Gly Ile
                805                 810                 815 att ttt gtg ctg ccc ttg ttt gtt gaa ata cca gct cat ctg cag tgg    2496
Ile Phe Val Leu Pro Leu Phe Val Glu Ile Pro Ala His Leu Gln Trp
            820                 825                 830 caa tgt gga gca att gct gtt tac ttc tat tgg atg aat ttc tta ttg    2544
Gln Cys Gly Ala Ile Ala Val Tyr Phe Tyr Trp Met Asn Phe Leu Leu
        835                 840                 845 tat ctt caa aga ttt gaa aat tgt gga att ttt att gtt atg ttg gag    2592
Tyr Leu Gln Arg Phe Glu Asn Cys Gly Ile Phe Ile Val Met Leu Glu
    850                 855                 860 gta att ttg aaa act ttg ttg agg tct aca gtt gta ttt atc ttc ctt    2640
Val Ile Leu Lys Thr Leu Leu Arg Ser Thr Val Val Phe Ile Phe Leu
865                 870                 875                 880 ctt ctg gct ttt gga ctc agc ttt tac atc ctc ctg aat tta cag gat    2688
Leu Leu Ala Phe Gly Leu Ser Phe Tyr Ile Leu Leu Asn Leu Gln Asp
                885                 890                 895 ccc ttc agc tct cca ttg ctt tct ata atc cag acc ttc agc atg atg    2736
Pro Phe Ser Ser Pro Leu Leu Ser Ile Ile Gln Thr Phe Ser Met Met
            900                 905                 910 cta gga gat atc aat tat cga gag tcc ttc cta gaa cca tat ctg aga    2784
Leu Gly Asp Ile Asn Tyr Arg Glu Ser Phe Leu Glu Pro Tyr Leu Arg
        915                 920                 925 aat gaa ttg gca cat cca gtt ctg tcc ttt gca caa ctt gtt tcc ttc    2832
Asn Glu Leu Ala His Pro Val Leu Ser Phe Ala Gln Leu Val Ser Phe
    930                 935                 940 aca ata ttt gtc cca att gtc ctc atg aat tta ctt att ggt ttg gca    2880
Thr Ile Phe Val Pro Ile Val Leu Met Asn Leu Leu Ile Gly Leu Ala
945                 950                 955                 960 gtt ggc gac att gct gag gtc cag aaa cat gca tca ttg aag agg ata    2928
Val Gly Asp Ile Ala Glu Val Gln Lys His Ala Ser Leu Lys Arg Ile
                965                 970                 975 gct atg cag gtg gaa ctt cat acc agc tta gag aag aag ctg cca ctt    2976
Ala Met Gln Val Glu Leu His Thr Ser Leu Glu Lys Lys Leu Pro Leu
            980                 985                 990 tgg ttt cta cgc aaa gtg gat cag aaa tcc acc atc gtg tat ccc aac    3024
Trp Phe Leu Arg Lys Val Asp Gln Lys Ser Thr Ile Val Tyr Pro Asn
        995                 1000                1005 aaa ccc aga tct ggt ggg atg tta ttc cat ata ttc tgt ttt tta        3069
Lys Pro Arg Ser Gly Gly Met Leu Phe His Ile Phe Cys Phe Leu
```

-continued

```
                 1010                1015                1020
ttt  tgc  act  ggg  gaa  ata  aga  caa  gaa  ata  cca  aat  gct  gat  aaa    3114
Phe  Cys  Thr  Gly  Glu  Ile  Arg  Gln  Glu  Ile  Pro  Asn  Ala  Asp  Lys
     1025                1030                1035 tct  tta  gaa  atg  gaa  ata  tta  aag  cag  aaa  tac  cgg  ctg  aag  gat    3159
Ser  Leu  Glu  Met  Glu  Ile  Leu  Lys  Gln  Lys  Tyr  Arg  Leu  Lys  Asp
     1040                1045                1050 ctt  act  ttt  ctc  ctg  gaa  aaa  cag  cat  gag  ctc  att  aaa  ctg  atc    3204
Leu  Thr  Phe  Leu  Leu  Glu  Lys  Gln  His  Glu  Leu  Ile  Lys  Leu  Ile
     1055                1060                1065 att  cag  aag  atg  gag  atc  atc  tct  gag  aca  gag  gat  gat  gat  agc    3249
Ile  Gln  Lys  Met  Glu  Ile  Ile  Ser  Glu  Thr  Glu  Asp  Asp  Asp  Ser
     1070                1075                1080 cat  tgt  tct  ttt  caa  gac  agg  ttt  aag  aaa  gag  cag  atg  gaa  caa    3294
His  Cys  Ser  Phe  Gln  Asp  Arg  Phe  Lys  Lys  Glu  Gln  Met  Glu  Gln
     1085                1090                1095 agg  aat  agc  aga  tgg  aat  act  gtg  ttg  aga  gca  gtc  aag  gca  aaa    3339
Arg  Asn  Ser  Arg  Trp  Asn  Thr  Val  Leu  Arg  Ala  Val  Lys  Ala  Lys
     1100                1105                1110 aca  cac  cat  ctt  gag  cct  tag                                             3360
Thr  His  His  Leu  Glu  Pro
     1115
```

<210> SEQ ID NO 2
<211> LENGTH: 1119
<212> TYPE: PRT
<213> ORGANISM: Homo sapiens

<400> SEQUENCE: 2

```
Met  Lys  Cys  Ser  Leu  Arg  Lys  Met  Trp  Arg  Pro  Gly  Glu  Lys  Glu
1                 5                  10                 15

Pro  Gln  Gly  Val  Val  Tyr  Glu  Asp  Val  Pro  Asp  Asp  Thr  Glu  Asp  Phe
                 20                  25                 30

Lys  Glu  Ser  Leu  Lys  Val  Val  Phe  Glu  Gly  Ser  Ala  Tyr  Gly  Leu  Gln
                 35                  40                 45

Asn  Phe  Asn  Lys  Gln  Lys  Lys  Leu  Lys  Thr  Cys  Asp  Asp  Met  Asp  Thr
 50                  55                  60

Phe  Phe  Leu  His  Tyr  Ala  Ala  Ala  Glu  Gly  Gln  Ile  Glu  Leu  Met  Glu
65                   70                  75                  80

Lys  Ile  Thr  Arg  Asp  Ser  Ser  Leu  Glu  Val  Leu  His  Glu  Met  Asp  Asp
                 85                  90                  95

Tyr  Gly  Asn  Thr  Pro  Leu  His  Cys  Ala  Val  Glu  Lys  Asn  Gln  Ile  Glu
                 100                 105                 110

Ser  Val  Lys  Phe  Leu  Leu  Ser  Arg  Gly  Ala  Asn  Pro  Asn  Leu  Arg  Asn
                 115                 120                 125

Phe  Asn  Met  Met  Ala  Pro  Leu  His  Ile  Ala  Val  Gln  Gly  Met  Asn  Asn
                 130                 135                 140

Glu  Val  Met  Lys  Val  Leu  Leu  Glu  His  Arg  Thr  Ile  Asp  Val  Asn  Leu
145                 150                 155                 160

Glu  Gly  Glu  Asn  Gly  Asn  Thr  Ala  Val  Ile  Ile  Ala  Cys  Thr  Thr  Asn
                 165                 170                 175

Asn  Ser  Glu  Ala  Leu  Gln  Ile  Leu  Leu  Asn  Lys  Gly  Ala  Lys  Pro  Cys
                 180                 185                 190

Lys  Ser  Asn  Lys  Trp  Gly  Cys  Phe  Pro  Ile  His  Gln  Ala  Ala  Phe  Ser
                 195                 200                 205

Gly  Ser  Lys  Glu  Cys  Met  Glu  Ile  Ile  Leu  Arg  Phe  Gly  Glu  Glu  His
                 210                 215                 220
```

```
Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
            245                 250                 255

Met Cys Leu Asp Asn Gly Ala Gln Ile Asp Pro Val Glu Lys Gly Arg
        260                 265                 270

Cys Thr Ala Ile His Phe Ala Ala Thr Gln Gly Ala Thr Glu Ile Val
    275                 280                 285

Lys Leu Met Ile Ser Ser Tyr Ser Gly Ser Val Asp Ile Val Asn Thr
290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365

Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
        435                 440                 445

Pro Leu His Phe Ala Ala Ser Tyr Gly Arg Ile Asn Thr Cys Gln Arg
    450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
        515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655
```

-continued

Glu Tyr Asn Phe Lys Tyr Leu Gln Cys Pro Leu Glu Phe Thr Lys Lys
                660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
                740                 745                 750

Asn Glu Thr Ser Asp His Ser Glu Ile Leu Asp Thr Thr Asn Ser Tyr
                755                 760                 765

Leu Ile Lys Thr Cys Met Ile Leu Val Phe Leu Ser Ser Ile Phe Gly
            770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
                820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
                915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
                980                 985                 990

Trp Phe Leu Arg Lys Val Asp Gln Lys Ser Thr Ile Val Tyr Pro Asn
            995                 1000                1005

Lys Pro Arg Ser Gly Gly Met Leu Phe His Ile Phe Cys Phe Leu
    1010                1015                1020

Phe Cys Thr Gly Glu Ile Arg Gln Glu Ile Pro Asn Ala Asp Lys
    1025                1030                1035

Ser Leu Glu Met Glu Ile Leu Lys Gln Lys Tyr Arg Leu Lys Asp
    1040                1045                1050

Leu Thr Phe Leu Leu Glu Lys Gln His Glu Leu Ile Lys Leu Ile
    1055                1060                1065

Ile Gln Lys Met Glu Ile Ile Ser Glu Thr Glu Asp Asp Asp Ser

```
                       1070              1075              1080
      His Cys Ser Phe Gln Asp Arg   Phe Lys Lys Glu Gln   Met Glu Gln
          1085              1090              1095

Arg Asn Ser Arg Trp Asn Thr   Val Leu Arg Ala Val   Lys Ala Lys
          1100              1105              1110

Thr His His Leu Glu Pro
          1115

<210> SEQ ID NO 3
<211> LENGTH: 3378
<212> TYPE: DNA
<213> ORGANISM: Mus musculus
<220> FEATURE:
<221> NAME/KEY: CDS
<222> LOCATION: (1)..(3378)

<400> SEQUENCE: 3 atg aag cgc ggc ttg agg agg att ctg ctc ccg gag gaa agg aag gag      48
Met Lys Arg Gly Leu Arg Arg Ile Leu Leu Pro Glu Glu Arg Lys Glu
  1               5                  10                  15 gtc cag ggc gtt gtc tat cgc ggc gtc ggg gaa gac atg gac tgc tcc      96
Val Gln Gly Val Val Tyr Arg Gly Val Gly Glu Asp Met Asp Cys Ser
             20                  25                  30 aag gaa tcc ttt aag gtg gac att gaa gga gat atg tgt aga tta gaa     144
Lys Glu Ser Phe Lys Val Asp Ile Glu Gly Asp Met Cys Arg Leu Glu
         35                  40                  45 gac ttc atc aag aac cga aga aaa cta agc aaa tat gag gat gaa aat     192
Asp Phe Ile Lys Asn Arg Arg Lys Leu Ser Lys Tyr Glu Asp Glu Asn
     50                  55                  60 ctc tgt cct ctg cat cac gca gca gca gaa ggt caa gtt gaa ctg atg     240
Leu Cys Pro Leu His His Ala Ala Ala Glu Gly Gln Val Glu Leu Met
 65                  70                  75                  80 gaa ctg atc atc aat ggt tct tcg tgt gaa gtg ctg aat ata atg gat     288
Glu Leu Ile Ile Asn Gly Ser Ser Cys Glu Val Leu Asn Ile Met Asp
                 85                  90                  95 ggt tat gga aat acc cca ctg cat tgt gct gca gaa aaa aat caa gtt     336
Gly Tyr Gly Asn Thr Pro Leu His Cys Ala Ala Glu Lys Asn Gln Val
            100                 105                 110 gaa agt gta aag ttt ctt ctc agc caa gga gca aat cca aac ctc cga     384
Glu Ser Val Lys Phe Leu Leu Ser Gln Gly Ala Asn Pro Asn Leu Arg
        115                 120                 125 aat aga aac atg atg tca ccc ctt cac ata gct gtg cat ggc atg tac     432
Asn Arg Asn Met Met Ser Pro Leu His Ile Ala Val His Gly Met Tyr
    130                 135                 140 aac gaa gtg atc aag gtg ttg act gag cac aag gcc act aac atc aat     480
Asn Glu Val Ile Lys Val Leu Thr Glu His Lys Ala Thr Asn Ile Asn
145                 150                 155                 160 tta gaa gga gag aat ggg aac acg gct ttg atg tcc acg tgt gcc aaa     528
Leu Glu Gly Glu Asn Gly Asn Thr Ala Leu Met Ser Thr Cys Ala Lys
                165                 170                 175 gac aac agt gaa gct ttg caa att ttg tta gaa aaa gga gct aag ctg     576
Asp Asn Ser Glu Ala Leu Gln Ile Leu Leu Glu Lys Gly Ala Lys Leu
            180                 185                 190 tgt aaa tca aat aag tgg gga gac tac cct gtg cac cag gca gca ttt     624
Cys Lys Ser Asn Lys Trp Gly Asp Tyr Pro Val His Gln Ala Ala Phe
        195                 200                 205 tca ggt gcc aaa aaa tgc atg gaa tta atc tta gca tat ggt gaa aag     672
Ser Gly Ala Lys Lys Cys Met Glu Leu Ile Leu Ala Tyr Gly Glu Lys
    210                 215                 220 aac ggc tac agc agg gag act cac att aat ttt gtg aat cac aag aaa     720
Asn Gly Tyr Ser Arg Glu Thr His Ile Asn Phe Val Asn His Lys Lys
```

```
                    225                 230                 235                 240
gcc agc cct ctc cac cta gca gtt caa agc gga gac ttg gac atg att        768
Ala Ser Pro Leu His Leu Ala Val Gln Ser Gly Asp Leu Asp Met Ile
                    245                 250                 255 aag atg tgc ctg gac aac ggt gca cac atc gac atg atg gag aat gcc        816
Lys Met Cys Leu Asp Asn Gly Ala His Ile Asp Met Met Glu Asn Ala
                    260                 265                 270 aaa tgc atg gcc ctc cat ttt gct gca acc cag gga gcc act gac atc        864
Lys Cys Met Ala Leu His Phe Ala Ala Thr Gln Gly Ala Thr Asp Ile
                275                 280                 285 gtt aag ctc atg atc tca tcc tat acc gga agt agt gat att gtg aat        912
Val Lys Leu Met Ile Ser Ser Tyr Thr Gly Ser Ser Asp Ile Val Asn
            290                 295                 300 gca gtt gat ggc aat cag gag acc ctg ctt cac aga gcc tcg tta ttt        960
Ala Val Asp Gly Asn Gln Glu Thr Leu Leu His Arg Ala Ser Leu Phe
305                 310                 315                 320 gat cac cat gac ctg gca gaa tac cta ata tca gtg gga gca gac atc       1008
Asp His His Asp Leu Ala Glu Tyr Leu Ile Ser Val Gly Ala Asp Ile
                    325                 330                 335 aac agc act gat tct gaa gga cgc tct cca ctt att tta gca aca gct       1056
Asn Ser Thr Asp Ser Glu Gly Arg Ser Pro Leu Ile Leu Ala Thr Ala
                340                 345                 350 tct gca tcc tgg aac att gtg aat ttg ctc ctc tgt aaa ggt gcc aaa       1104
Ser Ala Ser Trp Asn Ile Val Asn Leu Leu Leu Cys Lys Gly Ala Lys
            355                 360                 365 gta gac ata aaa gat cat ctt gga cgt aac ttt ttg cat ttg act gtg       1152
Val Asp Ile Lys Asp His Leu Gly Arg Asn Phe Leu His Leu Thr Val
370                 375                 380 cag cag cct tat gga cta aga aat ttg cgg cct gag ttt atg cag atg       1200
Gln Gln Pro Tyr Gly Leu Arg Asn Leu Arg Pro Glu Phe Met Gln Met
385                 390                 395                 400 caa cac atc aaa gag ctg gtg atg gat gaa gac aat gac gga tgc aca       1248
Gln His Ile Lys Glu Leu Val Met Asp Glu Asp Asn Asp Gly Cys Thr
                    405                 410                 415 cct ctc cat tat gcc tgt agg cag ggg gtt cct gtc tct gta aat aac       1296
Pro Leu His Tyr Ala Cys Arg Gln Gly Val Pro Val Ser Val Asn Asn
                420                 425                 430 ctc ctt ggc ttc aat gtg tcc att cat agc aaa agt aaa gat aag aag       1344
Leu Leu Gly Phe Asn Val Ser Ile His Ser Lys Ser Lys Asp Lys Lys
            435                 440                 445 tcg ccc ctg cat ttt gca gcc agt tat ggg cgc atc aat aca tgt cag       1392
Ser Pro Leu His Phe Ala Ala Ser Tyr Gly Arg Ile Asn Thr Cys Gln
450                 455                 460 aga ctt ctg caa gac ata agt gat acg agg ctt ttg aat gaa ggg gat       1440
Arg Leu Leu Gln Asp Ile Ser Asp Thr Arg Leu Leu Asn Glu Gly Asp
465                 470                 475                 480 ctc cat ggg atg acc cct ctc cac ctg gca gca aaa aat ggg cat gat       1488
Leu His Gly Met Thr Pro Leu His Leu Ala Ala Lys Asn Gly His Asp
                    485                 490                 495 aaa gtc gtt caa ctc ctt ctg aag aaa ggg gcc tta ttt ctc agt gac       1536
Lys Val Val Gln Leu Leu Leu Lys Lys Gly Ala Leu Phe Leu Ser Asp
                500                 505                 510 cac aat ggc tgg act gct ttg cat cac gcc tcc atg ggt ggg tac act       1584
His Asn Gly Trp Thr Ala Leu His His Ala Ser Met Gly Gly Tyr Thr
            515                 520                 525 cag acc atg aag gtc att ctt gat act aac ttg aaa tgc aca gac cga       1632
Gln Thr Met Lys Val Ile Leu Asp Thr Asn Leu Lys Cys Thr Asp Arg
530                 535                 540 cta gat gaa gaa ggg aac aca gca ctc cac ttt gca gca cgg gaa ggc       1680
Leu Asp Glu Glu Gly Asn Thr Ala Leu His Phe Ala Ala Arg Glu Gly
```

```
              545                 550                 555                 560 cat gcc aag gct gtt gca atg ctt ttg agc tac aat gct gac atc ctc          1728
His Ala Lys Ala Val Ala Met Leu Leu Ser Tyr Asn Ala Asp Ile Leu
                565                 570                 575 ctg aac aag aag caa gct tcc ttt ctg cat att gcc ctg cac aat aag          1776
Leu Asn Lys Lys Gln Ala Ser Phe Leu His Ile Ala Leu His Asn Lys
            580                 585                 590 cgc aag gaa gtg gtt ctc aca acc atc aga aat aaa aga tgg gat gag          1824
Arg Lys Glu Val Val Leu Thr Thr Ile Arg Asn Lys Arg Trp Asp Glu
        595                 600                 605 tgt ctt caa gtt ttc act cat aat tct cca agc aat cga tgt cca atc          1872
Cys Leu Gln Val Phe Thr His Asn Ser Pro Ser Asn Arg Cys Pro Ile
    610                 615                 620 atg gag atg gta gaa tac ctc ccc gag tgc atg aaa gtt ctt tta gat          1920
Met Glu Met Val Glu Tyr Leu Pro Glu Cys Met Lys Val Leu Leu Asp
625                 630                 635                 640 ttc tgc atg ata cct tcc aca gaa gac aag tcc tgt caa gac tac cat          1968
Phe Cys Met Ile Pro Ser Thr Glu Asp Lys Ser Cys Gln Asp Tyr His
                645                 650                 655 att gag tat aat ttc aag tat ctc caa tgc cca tta tcc atg acc aaa          2016
Ile Glu Tyr Asn Phe Lys Tyr Leu Gln Cys Pro Leu Ser Met Thr Lys
            660                 665                 670 aaa gta gca cct acc cag gat gtg gta tat gag cct ctt aca atc ctc          2064
Lys Val Ala Pro Thr Gln Asp Val Val Tyr Glu Pro Leu Thr Ile Leu
        675                 680                 685 aat gtc atg gtc caa cat aac cgc ata gaa ctc ctc aac cac cct gtg          2112
Asn Val Met Val Gln His Asn Arg Ile Glu Leu Leu Asn His Pro Val
    690                 695                 700 tgt agg gag tac tta ctc atg aaa tgg tgt gcc tat gga ttc aga gcc          2160
Cys Arg Glu Tyr Leu Leu Met Lys Trp Cys Ala Tyr Gly Phe Arg Ala
705                 710                 715                 720 cat atg atg aac cta gga tct tat tgt ctt ggt ctc ata ccc atg acc          2208
His Met Met Asn Leu Gly Ser Tyr Cys Leu Gly Leu Ile Pro Met Thr
                725                 730                 735 ctt ctt gtt gtc aaa ata cag cct gga atg gcc ttc aat tct act gga          2256
Leu Leu Val Val Lys Ile Gln Pro Gly Met Ala Phe Asn Ser Thr Gly
            740                 745                 750 ata atc aat gga act agt agt act cat gag gaa aga ata gac act ctg          2304
Ile Ile Asn Gly Thr Ser Ser Thr His Glu Glu Arg Ile Asp Thr Leu
        755                 760                 765 aat tca ttt cca ata aaa ata tgt atg att cta gtt ttt tta tca agt          2352
Asn Ser Phe Pro Ile Lys Ile Cys Met Ile Leu Val Phe Leu Ser Ser
    770                 775                 780 ata ttt gga tat tgc aaa gaa gtg atc caa att ttc caa cag aaa agg          2400
Ile Phe Gly Tyr Cys Lys Glu Val Ile Gln Ile Phe Gln Gln Lys Arg
785                 790                 795                 800 aat tac ttc ctg gat tac aac aat gct ctg gaa tgg gtt atc tat aca          2448
Asn Tyr Phe Leu Asp Tyr Asn Asn Ala Leu Glu Trp Val Ile Tyr Thr
                805                 810                 815 act agt atc atc ttc gtg ttg ccc ttg ttc ctc aac atc cca gcg tat          2496
Thr Ser Ile Ile Phe Val Leu Pro Leu Phe Leu Asn Ile Pro Ala Tyr
            820                 825                 830 atg cag tgg caa tgt gga gca ata gcg ata ttc ttc tac tgg atg aac          2544
Met Gln Trp Gln Cys Gly Ala Ile Ala Ile Phe Phe Tyr Trp Met Asn
        835                 840                 845 ttc cta ctg tat ctt caa agg ttt gag aac tgt gga att ttc att gtt          2592
Phe Leu Leu Tyr Leu Gln Arg Phe Glu Asn Cys Gly Ile Phe Ile Val
    850                 855                 860 atg ttg gag gtg att ttt aaa aca ttg ctg aga tcg acc gga gtg ttt          2640
Met Leu Glu Val Ile Phe Lys Thr Leu Leu Arg Ser Thr Gly Val Phe
```

```
                865                  870                  875                  880
atc ttc ctc cta ctg gct ttt ggc ctc agc ttt tat gtt ctc ctg aat           2688
Ile Phe Leu Leu Leu Ala Phe Gly Leu Ser Phe Tyr Val Leu Leu Asn
                    885                  890                  895 ttc caa gat gcc ttc agc acc cca ttg ctt tcc tta atc cag aca ttc           2736
Phe Gln Asp Ala Phe Ser Thr Pro Leu Leu Ser Leu Ile Gln Thr Phe
                900                  905                  910 agt atg atg cta gga gac atc aat tat cga gat gcc ttc cta gaa cca           2784
Ser Met Met Leu Gly Asp Ile Asn Tyr Arg Asp Ala Phe Leu Glu Pro
            915                  920                  925 ttg ttt aga aat gag ttg gca tac cca gtc ctg acc ttt ggg cag ctt           2832
Leu Phe Arg Asn Glu Leu Ala Tyr Pro Val Leu Thr Phe Gly Gln Leu
        930                  935                  940 att gcc ttc aca atg ttt gtc cca att gtt ctc atg aac tta ctg att           2880
Ile Ala Phe Thr Met Phe Val Pro Ile Val Leu Met Asn Leu Leu Ile
945                  950                  955                  960 ggc ttg gcg gtt ggg gac att gct gag gtc cag aag cat gcg tca ttg           2928
Gly Leu Ala Val Gly Asp Ile Ala Glu Val Gln Lys His Ala Ser Leu
                965                  970                  975 aag agg att gct atg cag gtg gaa ctt cat acc aac tta gaa aaa aag           2976
Lys Arg Ile Ala Met Gln Val Glu Leu His Thr Asn Leu Glu Lys Lys
            980                  985                  990 ctg cca ctc tgg tac tta cgc aaa  gtg gat cag agg tcc  acc atc gtg         3024
Leu Pro Leu Trp Tyr Leu Arg Lys  Val Asp Gln Arg Ser  Thr Ile Val
        995                  1000                  1005 tat cca aat aga ccc agg cac  ggc agg atg cta cgg  ttt ttt cat             3069
Tyr Pro Asn Arg Pro Arg His  Gly Arg Met Leu Arg  Phe Phe His
    1010                  1015                  1020 tac ttt ctt aat atg caa gaa  aca cga caa gaa gta  cca aac att             3114
Tyr Phe Leu Asn Met Gln Glu  Thr Arg Gln Glu Val  Pro Asn Ile
    1025                  1030                  1035 gac aca tgc ttg gaa atg gaa  ata ttg aaa cag aaa  tat cgg ctg             3159
Asp Thr Cys Leu Glu Met Glu  Ile Leu Lys Gln Lys  Tyr Arg Leu
    1040                  1045                  1050 aag gac ctc act tcc ctc ttg  gaa aag cag cat gag  ctc atc aaa             3204
Lys Asp Leu Thr Ser Leu Leu  Glu Lys Gln His Glu  Leu Ile Lys
    1055                  1060                  1065 ctc atc atc cag aag atg gag  atc atc tca gag aca  gaa gat gaa             3249
Leu Ile Ile Gln Lys Met Glu  Ile Ile Ser Glu Thr  Glu Asp Glu
    1070                  1075                  1080 gat aac cat tgc tct ttc caa  gac agg ttc aag aag  gag agg ctg             3294
Asp Asn His Cys Ser Phe Gln  Asp Arg Phe Lys Lys  Glu Arg Leu
    1085                  1090                  1095 gaa cag atg cac agc aag tgg  aat ttt gtc tta aac  gca gtt aag             3339
Glu Gln Met His Ser Lys Trp  Asn Phe Val Leu Asn  Ala Val Lys
    1100                  1105                  1110 act aaa aca cat tgt tct att  agc cac ccg gac ttt  tag                     3378
Thr Lys Thr His Cys Ser Ile  Ser His Pro Asp Phe
    1115                  1120                  1125

<210> SEQ ID NO 4
<211> LENGTH: 1125
<212> TYPE: PRT
<213> ORGANISM: Mus musculus

<400> SEQUENCE: 4

Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
            20                  25                  30
```

```
Lys Glu Ser Phe Lys Val Asp Ile Glu Gly Asp Met Cys Arg Leu Glu
         35                  40                  45

Asp Phe Ile Lys Asn Arg Arg Lys Leu Ser Lys Tyr Glu Asp Glu Asn
 50                  55                  60

Leu Cys Pro Leu His His Ala Ala Glu Gly Gln Val Glu Leu Met
 65                  70                  75                  80

Glu Leu Ile Ile Asn Gly Ser Ser Cys Glu Val Leu Asn Ile Met Asp
                 85                  90                  95

Gly Tyr Gly Asn Thr Pro Leu His Cys Ala Ala Glu Lys Asn Gln Val
             100                 105                 110

Glu Ser Val Lys Phe Leu Leu Ser Gln Gly Ala Asn Pro Asn Leu Arg
         115                 120                 125

Asn Arg Asn Met Met Ser Pro Leu His Ile Ala Val His Gly Met Tyr
 130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                 165                 170                 175

Asp Asn Ser Glu Ala Leu Gln Ile Leu Leu Glu Lys Gly Ala Lys Leu
             180                 185                 190

Cys Lys Ser Asn Lys Trp Gly Asp Tyr Pro Val His Gln Ala Ala Phe
         195                 200                 205

Ser Gly Ala Lys Lys Cys Met Glu Leu Ile Leu Ala Tyr Gly Glu Lys
 210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                 245                 250                 255

Lys Met Cys Leu Asp Asn Gly Ala His Ile Asp Met Met Glu Asn Ala
             260                 265                 270

Lys Cys Met Ala Leu His Phe Ala Ala Thr Gln Gly Ala Thr Asp Ile
         275                 280                 285

Val Lys Leu Met Ile Ser Ser Tyr Thr Gly Ser Ser Asp Ile Val Asn
 290                 295                 300

Ala Val Asp Gly Asn Gln Glu Thr Leu Leu His Arg Ala Ser Leu Phe
305                 310                 315                 320

Asp His His Asp Leu Ala Glu Tyr Leu Ile Ser Val Gly Ala Asp Ile
                 325                 330                 335

Asn Ser Thr Asp Ser Glu Gly Arg Ser Pro Leu Ile Leu Ala Thr Ala
             340                 345                 350

Ser Ala Ser Trp Asn Ile Val Asn Leu Leu Leu Cys Lys Gly Ala Lys
         355                 360                 365

Val Asp Ile Lys Asp His Leu Gly Arg Asn Phe Leu His Leu Thr Val
 370                 375                 380

Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
                 405                 410                 415

Pro Leu His Tyr Ala Cys Arg Gln Gly Val Pro Val Ser Val Asn Asn
             420                 425                 430

Leu Leu Gly Phe Asn Val Ser Ile His Ser Lys Ser Lys Asp Lys Lys
         435                 440                 445

Ser Pro Leu His Phe Ala Ala Ser Tyr Gly Arg Ile Asn Thr Cys Gln
 450                 455                 460
```

-continued

```
Arg Leu Leu Gln Asp Ile Ser Asp Thr Arg Leu Leu Asn Glu Gly Asp
465                 470                 475                 480
Leu His Gly Met Thr Pro Leu His Leu Ala Ala Lys Asn Gly His Asp
            485                 490                 495
Lys Val Val Gln Leu Leu Lys Gly Ala Leu Phe Leu Ser Asp
        500                 505                 510
His Asn Gly Trp Thr Ala Leu His His Ala Ser Met Gly Gly Tyr Thr
            515                 520                 525
Gln Thr Met Lys Val Ile Leu Asp Thr Asn Leu Lys Cys Thr Asp Arg
        530                 535                 540
Leu Asp Glu Glu Gly Asn Thr Ala Leu His Phe Ala Ala Arg Glu Gly
545                 550                 555                 560
His Ala Lys Ala Val Ala Met Leu Leu Ser Tyr Asn Ala Asp Ile Leu
                565                 570                 575
Leu Asn Lys Lys Gln Ala Ser Phe Leu His Ile Ala Leu His Asn Lys
            580                 585                 590
Arg Lys Glu Val Val Leu Thr Thr Ile Arg Asn Lys Arg Trp Asp Glu
        595                 600                 605
Cys Leu Gln Val Phe Thr His Asn Ser Pro Ser Asn Arg Cys Pro Ile
610                 615                 620
Met Glu Met Val Glu Tyr Leu Pro Glu Cys Met Lys Val Leu Leu Asp
625                 630                 635                 640
Phe Cys Met Ile Pro Ser Thr Glu Asp Lys Ser Cys Gln Asp Tyr His
                645                 650                 655
Ile Glu Tyr Asn Phe Lys Tyr Leu Gln Cys Pro Leu Ser Met Thr Lys
            660                 665                 670
Lys Val Ala Pro Thr Gln Asp Val Val Tyr Glu Pro Leu Thr Ile Leu
        675                 680                 685
Asn Val Met Val Gln His Asn Arg Ile Glu Leu Leu Asn His Pro Val
690                 695                 700
Cys Arg Glu Tyr Leu Leu Met Lys Trp Cys Ala Tyr Gly Phe Arg Ala
705                 710                 715                 720
His Met Met Asn Leu Gly Ser Tyr Cys Leu Gly Leu Ile Pro Met Thr
                725                 730                 735
Leu Leu Val Val Lys Ile Gln Pro Gly Met Ala Phe Asn Ser Thr Gly
            740                 745                 750
Ile Ile Asn Gly Thr Ser Ser Thr His Glu Glu Arg Ile Asp Thr Leu
        755                 760                 765
Asn Ser Phe Pro Ile Lys Ile Cys Met Ile Leu Val Phe Leu Ser Ser
770                 775                 780
Ile Phe Gly Tyr Cys Lys Glu Val Ile Gln Ile Phe Gln Gln Lys Arg
785                 790                 795                 800
Asn Tyr Phe Leu Asp Tyr Asn Asn Ala Leu Glu Trp Val Ile Tyr Thr
                805                 810                 815
Thr Ser Ile Ile Phe Val Leu Pro Leu Phe Leu Asn Ile Pro Ala Tyr
            820                 825                 830
Met Gln Trp Gln Cys Gly Ala Ile Ala Ile Phe Phe Tyr Trp Met Asn
        835                 840                 845
Phe Leu Leu Tyr Leu Gln Arg Phe Glu Asn Cys Gly Ile Phe Ile Val
850                 855                 860
Met Leu Glu Val Ile Phe Lys Thr Leu Arg Ser Thr Gly Val Phe
865                 870                 875                 880
Ile Phe Leu Leu Leu Ala Phe Gly Leu Ser Phe Tyr Val Leu Leu Asn
```

```
                        885                 890                 895
Phe Gln Asp Ala Phe Ser Thr Pro Leu Leu Ser Leu Ile Gln Thr Phe
                900                 905                 910
Ser Met Met Leu Gly Asp Ile Asn Tyr Arg Asp Ala Phe Leu Glu Pro
                915                 920                 925
Leu Phe Arg Asn Glu Leu Ala Tyr Pro Val Leu Thr Phe Gly Gln Leu
                930                 935                 940
Ile Ala Phe Thr Met Phe Val Pro Ile Val Leu Met Asn Leu Leu Ile
945                 950                 955                 960
Gly Leu Ala Val Gly Asp Ile Ala Glu Val Gln Lys His Ala Ser Leu
                965                 970                 975
Lys Arg Ile Ala Met Gln Val Glu Leu His Thr Asn Leu Glu Lys Lys
                980                 985                 990
Leu Pro Leu Trp Tyr Leu Arg Lys  Val Asp Gln Arg Ser  Thr Ile Val
                995                 1000                1005
Tyr Pro  Asn Arg Pro Arg His  Gly Arg Met Leu Arg  Phe Phe His
    1010                1015                1020
Tyr Phe  Leu Asn Met Gln Glu  Thr Arg Gln Glu Val  Pro Asn Ile
    1025                1030                1035
Asp Thr  Cys Leu Glu Met Glu  Ile Leu Lys Gln Lys  Tyr Arg Leu
    1040                1045                1050
Lys Asp  Leu Thr Ser Leu Leu  Glu Lys Gln His Glu  Leu Ile Lys
    1055                1060                1065
Leu Ile  Ile Gln Lys Met Glu  Ile Ile Ser Glu Thr  Glu Asp Glu
    1070                1075                1080
Asp Asn  His Cys Ser Phe Gln  Asp Arg Phe Lys Lys  Glu Arg Leu
    1085                1090                1095
Glu Gln  Met His Ser Lys Trp  Asn Phe Val Leu Asn  Ala Val Lys
    1100                1105                1110
Thr Lys  Thr His Cys Ser Ile  Ser His Pro Asp Phe
    1115                1120                1125

<210> SEQ ID NO 5
<211> LENGTH: 3378
<212> TYPE: DNA
<213> ORGANISM: Rattus norvegicus
<220> FEATURE:
<221> NAME/KEY: CDS
<222> LOCATION: (1)..(3378)

<400> SEQUENCE: 5 atg aag cgc agc ttg agg agg gtt ctg cgc ccc gag gaa aga aag gag      48
Met Lys Arg Ser Leu Arg Arg Val Leu Arg Pro Glu Glu Arg Lys Glu
1               5                   10                  15 gtc cag ggc gtc gtc tat cgc ggc gtg ggg aaa gac atg gac tgc tcc      96
Val Gln Gly Val Val Tyr Arg Gly Val Gly Lys Asp Met Asp Cys Ser
            20                  25                  30 aag gaa tcc ttt aag gtg gac att gaa gga gat atg tgc aga tta gaa     144
Lys Glu Ser Phe Lys Val Asp Ile Glu Gly Asp Met Cys Arg Leu Glu
        35                  40                  45 gcc ttc atc aag aac cga aga aaa cta agc aag tac gag gat gaa aat     192
Ala Phe Ile Lys Asn Arg Arg Lys Leu Ser Lys Tyr Glu Asp Glu Asn
    50                  55                  60 ctc tgt ctt ctg cat cac gcc gca gcc gaa ggt caa gtt gaa ctg atg     240
Leu Cys Leu Leu His His Ala Ala Ala Glu Gly Gln Val Glu Leu Met
65                  70                  75                  80 caa ttg atc atc aat ggc tct tcc tgt gaa gcg ctg aat gta atg gat     288
Gln Leu Ile Ile Asn Gly Ser Ser Cys Glu Ala Leu Asn Val Met Asp
```

-continued

```
                     85                  90                  95
gat tat gga aat acc cca cta cat tgg gct gca gaa aaa aat caa gtt      336
Asp Tyr Gly Asn Thr Pro Leu His Trp Ala Ala Glu Lys Asn Gln Val
            100                 105                 110 gaa agt gtg aag ttt ctt ctc agc caa gga gca aat cca aac ctc cga      384
Glu Ser Val Lys Phe Leu Leu Ser Gln Gly Ala Asn Pro Asn Leu Arg
        115                 120                 125 aat aga aac atg atg gca ccc ctt cac ata gct gta cag ggc atg tac      432
Asn Arg Asn Met Met Ala Pro Leu His Ile Ala Val Gln Gly Met Tyr
130                 135                 140 aac gaa gtg atc aag gtc ttg acc gag cac aag gcc act aac atc aat      480
Asn Glu Val Ile Lys Val Leu Thr Glu His Lys Ala Thr Asn Ile Asn
145                 150                 155                 160 tta gaa gga gag aat ggg aac aca gct ttg atg tcc acg tgt gcc aaa      528
Leu Glu Gly Glu Asn Gly Asn Thr Ala Leu Met Ser Thr Cys Ala Lys
                165                 170                 175 gac aac agt gaa gct ttg caa att ttg tta gaa aaa gga gct aag ctg      576
Asp Asn Ser Glu Ala Leu Gln Ile Leu Leu Glu Lys Gly Ala Lys Leu
            180                 185                 190 tgt aaa tca aat aaa tgg gga gac tac cct gtg cac cag gca gca ttt      624
Cys Lys Ser Asn Lys Trp Gly Asp Tyr Pro Val His Gln Ala Ala Phe
        195                 200                 205 tca ggt gcc aaa aga tgc atg gaa tta atc tta gca tat ggt gaa aag      672
Ser Gly Ala Lys Arg Cys Met Glu Leu Ile Leu Ala Tyr Gly Glu Lys
210                 215                 220 acc ggc tat agc cgg gag gct cac att aac ttt gtg aat cat aag aaa      720
Thr Gly Tyr Ser Arg Glu Ala His Ile Asn Phe Val Asn His Lys Lys
225                 230                 235                 240 gcc agc cct ctc cac ctc gca gtt cag agc ggc gac ttg gac atg att      768
Ala Ser Pro Leu His Leu Ala Val Gln Ser Gly Asp Leu Asp Met Ile
                245                 250                 255 aag atg tgc ctg gac agc ggt gca cac atc gac atg atg gag aat gcc      816
Lys Met Cys Leu Asp Ser Gly Ala His Ile Asp Met Met Glu Asn Ala
            260                 265                 270 aaa tgc atg gcc ctc cat ttt gct gca acc cag gga gcc act gac atc      864
Lys Cys Met Ala Leu His Phe Ala Ala Thr Gln Gly Ala Thr Asp Ile
        275                 280                 285 gtt aaa ctc atg atc tca tcc tat act gga agc agc gat atc gtg aat      912
Val Lys Leu Met Ile Ser Ser Tyr Thr Gly Ser Ser Asp Ile Val Asn
290                 295                 300 gca gtc gat ggc aat cag gag acc ctg ctt cac aga gcc tca tta ttt      960
Ala Val Asp Gly Asn Gln Glu Thr Leu Leu His Arg Ala Ser Leu Phe
305                 310                 315                 320 gat cat cat gac ctg gca gac tac cta att tca gtg gga gca gac atc     1008
Asp His His Asp Leu Ala Asp Tyr Leu Ile Ser Val Gly Ala Asp Ile
                325                 330                 335 aac agc act gat tct gaa gga cgc tct cca ctt att tta gca act gct     1056
Asn Ser Thr Asp Ser Glu Gly Arg Ser Pro Leu Ile Leu Ala Thr Ala
            340                 345                 350 tct gca tcc tgg aat att gtg aat ttg ctc ctc tct aaa ggt gcc aaa     1104
Ser Ala Ser Trp Asn Ile Val Asn Leu Leu Leu Ser Lys Gly Ala Lys
        355                 360                 365 gta gac ata aaa gat cat ctt ggg cgt aac ttt tta cat ttg act gtg     1152
Val Asp Ile Lys Asp His Leu Gly Arg Asn Phe Leu His Leu Thr Val
370                 375                 380 cag cag cct tat ggg cta agg aat ttg cgg cct gag ttt ttg cag atg     1200
Gln Gln Pro Tyr Gly Leu Arg Asn Leu Arg Pro Glu Phe Leu Gln Met
385                 390                 395                 400 caa cac atc aag gag ctg gtg atg gat gag gac aat gat gga tgt acg     1248
Gln His Ile Lys Glu Leu Val Met Asp Glu Asp Asn Asp Gly Cys Thr
```

```
                    405                 410                 415
cct ctc cat tat gct tgt agg cag ggg gcc cct gtc tct gta aat aac      1296
Pro Leu His Tyr Ala Cys Arg Gln Gly Ala Pro Val Ser Val Asn Asn
            420                 425                 430 ctc ctc agg ttc aat gtg tcc gtt cat tcc aaa agc aaa gat aag aag      1344
Leu Leu Arg Phe Asn Val Ser Val His Ser Lys Ser Lys Asp Lys Lys
            435                 440                 445 tct ccc ctg cac ttt gcc gcc agc tat ggg cgc atc aat aca tgt cag      1392
Ser Pro Leu His Phe Ala Ala Ser Tyr Gly Arg Ile Asn Thr Cys Gln
450                 455                 460 agg ctt ctg caa gac atc agc gac aca agg ctt ttg aat gaa ggg gat      1440
Arg Leu Leu Gln Asp Ile Ser Asp Thr Arg Leu Leu Asn Glu Gly Asp
465                 470                 475                 480 ctc cat gga atg acc cct ctc cat ctg gca gca aag aat gga cat gat      1488
Leu His Gly Met Thr Pro Leu His Leu Ala Ala Lys Asn Gly His Asp
                485                 490                 495 aaa gtc gtt caa ctt ctt ctc aag aaa ggg gcc ttg ttt ctt agt gac      1536
Lys Val Val Gln Leu Leu Leu Lys Lys Gly Ala Leu Phe Leu Ser Asp
            500                 505                 510 cac aat ggc tgg act gct ttg cat cat gcg tcc atg ggt ggc tac act      1584
His Asn Gly Trp Thr Ala Leu His His Ala Ser Met Gly Gly Tyr Thr
            515                 520                 525 cag acc atg aag gtc att ctt gac act aac ttg aag tgc aca gac cgg      1632
Gln Thr Met Lys Val Ile Leu Asp Thr Asn Leu Lys Cys Thr Asp Arg
530                 535                 540 cta gat gaa gaa ggg aac aca gca ctt cac ttt gca gca cgg gaa ggc      1680
Leu Asp Glu Glu Gly Asn Thr Ala Leu His Phe Ala Ala Arg Glu Gly
545                 550                 555                 560 cat gca aag gct gtt gcg atg ctt ttg agc tac aat gct gac atc ctc      1728
His Ala Lys Ala Val Ala Met Leu Leu Ser Tyr Asn Ala Asp Ile Leu
                565                 570                 575 ctg aac aag aag caa gct tcc ttt ctg cat att gca ctg cac aat aag      1776
Leu Asn Lys Lys Gln Ala Ser Phe Leu His Ile Ala Leu His Asn Lys
            580                 585                 590 cgc aag gaa gtg gtt ctc aca acc atc agg agt aaa aga tgg gat gag      1824
Arg Lys Glu Val Val Leu Thr Thr Ile Arg Ser Lys Arg Trp Asp Glu
            595                 600                 605 tgt ctt caa gtt ttt act cat gat tct cca agc aat cgc tgt cca atc      1872
Cys Leu Gln Val Phe Thr His Asp Ser Pro Ser Asn Arg Cys Pro Ile
610                 615                 620 atg gaa atg gtg gaa tac ctc ccc gag tgc atg aaa gtt ctt cta gat      1920
Met Glu Met Val Glu Tyr Leu Pro Glu Cys Met Lys Val Leu Leu Asp
625                 630                 635                 640 ttc tgc atg ata cct tcc aca gaa gac aag tcc tgc caa gac tac cat      1968
Phe Cys Met Ile Pro Ser Thr Glu Asp Lys Ser Cys Gln Asp Tyr His
                645                 650                 655 att gag tat aat ttc aag tat ctc caa tgc cca tta tcc atg acc aaa      2016
Ile Glu Tyr Asn Phe Lys Tyr Leu Gln Cys Pro Leu Ser Met Thr Lys
            660                 665                 670 aaa gta acc ccc acc cag gat gtg atc tat gag cct ctt aca atc ctc      2064
Lys Val Thr Pro Thr Gln Asp Val Ile Tyr Glu Pro Leu Thr Ile Leu
            675                 680                 685 aat gtc atg gtc caa cat aac cgc ata gag ctc ctc aac cac cct gtg      2112
Asn Val Met Val Gln His Asn Arg Ile Glu Leu Leu Asn His Pro Val
690                 695                 700 tgt agg gaa tac tta ctt atg aaa tgg tgt gcc tat ggc ttc aga gct      2160
Cys Arg Glu Tyr Leu Leu Met Lys Trp Cys Ala Tyr Gly Phe Arg Ala
705                 710                 715                 720 cat atg atg aac cta gga tct tat tgt ctt ggt ctc ata ccc atg acc      2208
His Met Met Asn Leu Gly Ser Tyr Cys Leu Gly Leu Ile Pro Met Thr
```

-continued 725              730              735
ctt ctt gtt gtc aaa ata cag cct gga atg gcc ttc aat tct act gga    2256
Leu Leu Val Val Lys Ile Gln Pro Gly Met Ala Phe Asn Ser Thr Gly
            740              745              750 ata atc aat gaa act att agt act cat gag gaa aga ata aac act ctg    2304
Ile Ile Asn Glu Thr Ile Ser Thr His Glu Glu Arg Ile Asn Thr Leu
        755              760              765 aat tcg ttt cca tta aaa ata tgt atg att cta gtt ttt tta tca agt    2352
Asn Ser Phe Pro Leu Lys Ile Cys Met Ile Leu Val Phe Leu Ser Ser
    770              775              780 ata ttt gga tat tgc aaa gaa gtg gtc caa att ttc caa cag aaa agg    2400
Ile Phe Gly Tyr Cys Lys Glu Val Val Gln Ile Phe Gln Gln Lys Arg
785              790              795              800 aac tac ttt ctg gac tac aac aat gct ctg gag tgg gtc atc tac acc    2448
Asn Tyr Phe Leu Asp Tyr Asn Asn Ala Leu Glu Trp Val Ile Tyr Thr
            805              810              815 acc agt atg atc ttc gtg ttg ccc tta ttc ctc gac atc ccc gcg tat    2496
Thr Ser Met Ile Phe Val Leu Pro Leu Phe Leu Asp Ile Pro Ala Tyr
        820              825              830 atg cag tgg caa tgt gga gcg ata gca ata ttc ttc tac tgg atg aac    2544
Met Gln Trp Gln Cys Gly Ala Ile Ala Ile Phe Phe Tyr Trp Met Asn
    835              840              845 ttc cta cta tat ctt caa agg ttt gag aac tgt ggc att ttc att gtt    2592
Phe Leu Leu Tyr Leu Gln Arg Phe Glu Asn Cys Gly Ile Phe Ile Val
850              855              860 atg ttg gag gtg att ttt aaa aca ttg ctg aga tcg acg gga gtg ttt    2640
Met Leu Glu Val Ile Phe Lys Thr Leu Leu Arg Ser Thr Gly Val Phe
865              870              875              880 atc ttc ctg cta ttg gct ttt ggc ctc agc ttt tac gtc ctc ctg aat    2688
Ile Phe Leu Leu Leu Ala Phe Gly Leu Ser Phe Tyr Val Leu Leu Asn
            885              890              895 ttc caa gat gcc ttc agc acc ccg ttg ctt tcc tta atc cag acg ttc    2736
Phe Gln Asp Ala Phe Ser Thr Pro Leu Leu Ser Leu Ile Gln Thr Phe
        900              905              910 agt atg atg ctg gga gac atc aat tac cga gat gct ttc cta gaa ccg    2784
Ser Met Met Leu Gly Asp Ile Asn Tyr Arg Asp Ala Phe Leu Glu Pro
    915              920              925 ttg ttc agg aat gag ttg gca tac ccg gtc ctc acc ttt ggg cag ctt    2832
Leu Phe Arg Asn Glu Leu Ala Tyr Pro Val Leu Thr Phe Gly Gln Leu
930              935              940 att gcc ttc aca atg ttc gtc cca att gtt ctc atg aac cta ctg att    2880
Ile Ala Phe Thr Met Phe Val Pro Ile Val Leu Met Asn Leu Leu Ile
945              950              955              960 ggt ttg gca gtt ggg gac att gct gag gtc cag aag cat gca tca tta    2928
Gly Leu Ala Val Gly Asp Ile Ala Glu Val Gln Lys His Ala Ser Leu
            965              970              975 aag agg att gct atg cag gtg gaa ctg cat acc aac tta gaa aaa aag    2976
Lys Arg Ile Ala Met Gln Val Glu Leu His Thr Asn Leu Glu Lys Lys
        980              985              990 cta cca ttc tgg tac ttg cgc aaa  gtg gat cag agg tcc  acc atc gtg   3024
Leu Pro Phe Trp Tyr Leu Arg Lys  Val Asp Gln Arg Ser  Thr Ile Val
    995              1000              1005 tat ccg  aat aga ccc agg cac  ggc agg atg ctg cgg  ttt ttt cat      3069
Tyr Pro  Asn Arg Pro Arg His  Gly Arg Met Leu Arg  Phe Phe His
    1010              1015              1020 tac ttt  ctt agt atg caa gaa  aca cga caa gaa gca  cca aac att      3114
Tyr Phe  Leu Ser Met Gln Glu  Thr Arg Gln Glu Ala  Pro Asn Ile
    1025              1030              1035 gac aca  tgt ttg gaa atg gaa  ata ctg aaa cag aaa  tac cgg ctg      3159
Asp Thr  Cys Leu Glu Met Glu  Ile Leu Lys Gln Lys  Tyr Arg Leu -continued

```
                  1040              1045               1050
aag gac ctc act tct ctt ttg gaa aag cag cac gag ctc atc aaa       3204
Lys Asp Leu Thr Ser Leu Leu Glu Lys Gln His Glu Leu Ile Lys
 1055                1060                1065 ctc atc atc caa aag atg gag atc atc tcg gag aca gaa gat gaa       3249
Leu Ile Ile Gln Lys Met Glu Ile Ile Ser Glu Thr Glu Asp Glu
 1070                1075                1080 gat aac cat tgc tct ttc caa gac agg ttc aaa aag gaa cgg cta       3294
Asp Asn His Cys Ser Phe Gln Asp Arg Phe Lys Lys Glu Arg Leu
 1085                1090                1095 gaa caa atg cat agc aaa tgg aat ttt gtc tta aac gca gtt aag       3339
Glu Gln Met His Ser Lys Trp Asn Phe Val Leu Asn Ala Val Lys
 1100                1105                1110 act aaa aca cat tgt tct att agc cac cca gac atc tag               3378
Thr Lys Thr His Cys Ser Ile Ser His Pro Asp Ile
 1115                1120                1125

<210> SEQ ID NO 6
<211> LENGTH: 1125
<212> TYPE: PRT
<213> ORGANISM: Rattus norvegicus

<400> SEQUENCE: 6

Met Lys Arg Ser Leu Arg Arg Val Leu Arg Pro Glu Glu Arg Lys Glu
 1               5                  10                  15

Val Gln Gly Val Val Tyr Arg Gly Val Gly Lys Asp Met Asp Cys Ser
                20                  25                  30

Lys Glu Ser Phe Lys Val Asp Ile Glu Gly Asp Met Cys Arg Leu Glu
             35                  40                  45

Ala Phe Ile Lys Asn Arg Arg Lys Leu Ser Lys Tyr Glu Asp Glu Asn
         50                  55                  60

Leu Cys Leu Leu His His Ala Ala Glu Gly Gln Val Glu Leu Met
 65                  70                  75                  80

Gln Leu Ile Ile Asn Gly Ser Ser Cys Glu Ala Leu Asn Val Met Asp
                 85                  90                  95

Asp Tyr Gly Asn Thr Pro Leu His Trp Ala Ala Glu Lys Asn Gln Val
            100                 105                 110

Glu Ser Val Lys Phe Leu Leu Ser Gln Gly Ala Asn Pro Asn Leu Arg
         115                 120                 125

Asn Arg Asn Met Met Ala Pro Leu His Ile Ala Val Gln Gly Met Tyr
     130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
         195                 200                 205

Ser Gly Ala Lys Arg Cys Met Glu Leu Ile Leu Ala Tyr Gly Glu Lys
     210                 215                 220

Thr Gly Tyr Ser Arg Glu Ala His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Ser Gly Ala His Ile Asp Met Met Glu Asn Ala
            260                 265                 270
```

-continued

```
Lys Cys Met Ala Leu His Phe Ala Ala Thr Gln Gly Ala Thr Asp Ile
        275                 280                 285

Val Lys Leu Met Ile Ser Ser Tyr Thr Gly Ser Ser Asp Ile Val Asn
290                 295                 300

Ala Val Asp Gly Asn Gln Glu Thr Leu Leu His Arg Ala Ser Leu Phe
305                 310                 315                 320

Asp His His Asp Leu Ala Asp Tyr Leu Ile Ser Val Gly Ala Asp Ile
                325                 330                 335

Asn Ser Thr Asp Ser Glu Gly Arg Ser Pro Leu Ile Leu Ala Thr Ala
                340                 345                 350

Ser Ala Ser Trp Asn Ile Val Asn Leu Leu Leu Ser Lys Gly Ala Lys
                355                 360                 365

Val Asp Ile Lys Asp His Leu Gly Arg Asn Phe Leu His Leu Thr Val
370                 375                 380

Gln Gln Pro Tyr Gly Leu Arg Asn Leu Arg Pro Glu Phe Leu Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Ala Pro Val Ser Val Asn Asn
                420                 425                 430

Leu Leu Arg Phe Asn Val Ser Val His Ser Lys Ser Lys Asp Lys Lys
                435                 440                 445

Ser Pro Leu His Phe Ala Ala Ser Tyr Gly Arg Ile Asn Thr Cys Gln
450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
                500                 505                 510

His Asn Gly Trp Thr Ala Leu His His Ala Ser Met Gly Gly Tyr Thr
                515                 520                 525

Gln Thr Met Lys Val Ile Leu Asp Thr Asn Leu Lys Cys Thr Asp Arg
530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
                580                 585                 590

Arg Lys Glu Val Val Leu Thr Thr Ile Arg Ser Lys Arg Trp Asp Glu
                595                 600                 605

Cys Leu Gln Val Phe Thr His Asp Ser Pro Ser Asn Arg Cys Pro Ile
610                 615                 620

Met Glu Met Val Glu Tyr Leu Pro Glu Cys Met Lys Val Leu Leu Asp
625                 630                 635                 640

Phe Cys Met Ile Pro Ser Thr Glu Asp Lys Ser Cys Gln Asp Tyr His
                645                 650                 655

Ile Glu Tyr Asn Phe Lys Tyr Leu Gln Cys Pro Leu Ser Met Thr Lys
                660                 665                 670

Lys Val Thr Pro Thr Gln Asp Val Ile Tyr Glu Pro Leu Thr Ile Leu
                675                 680                 685

Asn Val Met Val Gln His Asn Arg Ile Glu Leu Leu Asn His Pro Val
```

-continued

```
              690                 695                 700
Cys Arg Glu Tyr Leu Leu Met Lys Trp Cys Ala Tyr Gly Phe Arg Ala
705                 710                 715                 720
His Met Met Asn Leu Gly Ser Tyr Cys Leu Gly Leu Ile Pro Met Thr
                725                 730                 735
Leu Leu Val Val Lys Ile Gln Pro Gly Met Ala Phe Asn Ser Thr Gly
                740                 745                 750
Ile Ile Asn Glu Thr Ile Ser Thr His Glu Arg Ile Asn Thr Leu
            755                 760                 765
Asn Ser Phe Pro Leu Lys Ile Cys Met Ile Leu Val Phe Leu Ser Ser
    770                 775                 780
Ile Phe Gly Tyr Cys Lys Glu Val Val Gln Ile Phe Gln Gln Lys Arg
785                 790                 795                 800
Asn Tyr Phe Leu Asp Tyr Asn Asn Ala Leu Glu Trp Val Ile Tyr Thr
                805                 810                 815
Thr Ser Met Ile Phe Val Leu Pro Leu Phe Leu Asp Ile Pro Ala Tyr
                820                 825                 830
Met Gln Trp Gln Cys Gly Ala Ile Ala Ile Phe Phe Tyr Trp Met Asn
            835                 840                 845
Phe Leu Leu Tyr Leu Gln Arg Phe Glu Asn Cys Gly Ile Phe Ile Val
850                 855                 860
Met Leu Glu Val Ile Phe Lys Thr Leu Leu Arg Ser Thr Gly Val Phe
865                 870                 875                 880
Ile Phe Leu Leu Leu Ala Phe Gly Leu Ser Phe Tyr Val Leu Leu Asn
                885                 890                 895
Phe Gln Asp Ala Phe Ser Thr Pro Leu Leu Ser Leu Ile Gln Thr Phe
            900                 905                 910
Ser Met Met Leu Gly Asp Ile Asn Tyr Arg Asp Ala Phe Leu Glu Pro
        915                 920                 925
Leu Phe Arg Asn Glu Leu Ala Tyr Pro Val Leu Thr Phe Gly Gln Leu
    930                 935                 940
Ile Ala Phe Thr Met Phe Val Pro Ile Val Leu Met Asn Leu Leu Ile
945                 950                 955                 960
Gly Leu Ala Val Gly Asp Ile Ala Glu Val Gln Lys His Ala Ser Leu
                965                 970                 975
Lys Arg Ile Ala Met Gln Val Glu Leu His Thr Asn Leu Glu Lys Lys
            980                 985                 990
Leu Pro Phe Trp Tyr Leu Arg Lys Val Asp Gln Arg Ser Thr Ile Val
        995                 1000                1005
Tyr Pro Asn Arg Pro Arg His Gly Arg Met Leu Arg Phe Phe His
    1010                1015                1020
Tyr Phe Leu Ser Met Gln Glu Thr Arg Gln Glu Ala Pro Asn Ile
    1025                1030                1035
Asp Thr Cys Leu Glu Met Glu Ile Leu Lys Gln Lys Tyr Arg Leu
    1040                1045                1050
Lys Asp Leu Thr Ser Leu Leu Glu Lys Gln His Glu Leu Ile Lys
    1055                1060                1065
Leu Ile Ile Gln Lys Met Glu Ile Ile Ser Glu Thr Glu Asp Glu
    1070                1075                1080
Asp Asn His Cys Ser Phe Gln Asp Arg Phe Lys Lys Glu Arg Leu
    1085                1090                1095
Glu Gln Met His Ser Lys Trp Asn Phe Val Leu Asn Ala Val Lys
    1100                1105                1110
```

```
        Thr Lys   Thr His Cys Ser Ile   Ser His Pro Asp Ile
            1115              1120              1125
```

```
<210> SEQ ID NO 7
<211> LENGTH: 18
<212> TYPE: DNA
<213> ORGANISM: Artificial
<220> FEATURE:
<223> OTHER INFORMATION: human TRPA1 primer-F

<400> SEQUENCE: 7
atgaagtgca gcctgagg                                                 18

<210> SEQ ID NO 8
<211> LENGTH: 18
<212> TYPE: DNA
<213> ORGANISM: Artificial
<220> FEATURE:
<223> OTHER INFORMATION: human TRPA1 primer-R

<400> SEQUENCE: 8
ctaaggctca agatggtg                                                 18

<210> SEQ ID NO 9
<211> LENGTH: 27
<212> TYPE: DNA
<213> ORGANISM: Artificial
<220> FEATURE:
<223> OTHER INFORMATION: human TRPA1 primer-2756F

<400> SEQUENCE: 9
gagagtcctt cctagaacca tatctga                                       27

<210> SEQ ID NO 10
<211> LENGTH: 25
<212> TYPE: DNA
<213> ORGANISM: Artificial
<220> FEATURE:
<223> OTHER INFORMATION: human TRPA1 primer-2859R

<400> SEQUENCE: 10
catgaggaca attgggacaa atatt                                         25

<210> SEQ ID NO 11
<211> LENGTH: 20
<212> TYPE: DNA
<213> ORGANISM: Artificial
<220> FEATURE:
<223> OTHER INFORMATION: mouse TRPA1 primer-308F

<400> SEQUENCE: 11
ctgcattgtg ctgcagaaaa                                               20

<210> SEQ ID NO 12
<211> LENGTH: 20
<212> TYPE: DNA
<213> ORGANISM: Artificial
<220> FEATURE:
<223> OTHER INFORMATION: mouse TRPA1 primer-381R

<400> SEQUENCE: 12
aggtttggat ttgctccttg                                               20

<210> SEQ ID NO 13
<211> LENGTH: 20
<212> TYPE: DNA
<213> ORGANISM: Artificial
```

```
<220> FEATURE:
<223> OTHER INFORMATION: rat TRPA1 primer-308F

<400> SEQUENCE: 13
ctacattggg ctgcagaaaa                                              20

<210> SEQ ID NO 14
<211> LENGTH: 20
<212> TYPE: DNA
<213> ORGANISM: Artificial
<220> FEATURE:
<223> OTHER INFORMATION: rat TRPA1 primer-381R

<400> SEQUENCE: 14
aggtttggat ttgctccttg                                              20

<210> SEQ ID NO 15
<211> LENGTH: 21
<212> TYPE: RNA
<213> ORGANISM: Artificial
<220> FEATURE:
<223> OTHER INFORMATION: rat TRPA1 primer-971-sense (for siRNA)

<400> SEQUENCE: 15
cuggcagacu accuaauuuc a                                            21

<210> SEQ ID NO 16
<211> LENGTH: 21
<212> TYPE: RNA
<213> ORGANISM: Artificial
<220> FEATURE:
<223> OTHER INFORMATION: rat TRPA1 primer-971-antisense (for siRNA)

<400> SEQUENCE: 16
aaauuaggua gucugccagg u                                            21
```

SCREENING METHOD FOR PROKINETIC AGENT

TECHNICAL FIELD

The present invention relates to a prophylactic and/or therapeutic drug for diseases associated with 5-HT production/secretion abnormalities, including digestive organ diseases, and a screening method and tool therefor and the like.

BACKGROUND ART

Serotonin (hereinafter referred to as 5-HT) is abundantly contained in fruits such as bananas, vegetables, harmful plants and the like. In animals, 90% of 5-HT in the living body is present in the gastrointestinal tract. The 5-HT in the gastrointestinal tract is biosynthesized in gastrointestinal mucosal chromaffin cells (enterochromaffin cells; hereinafter referred to as EC cells), entering the blood circulation, and is transported to the whole body. The 5-HT released upon chemical stimulation or mechanical stimulation of the gut binds to 5-HT receptors of target cells to cause physiological reactions. As 5-HT receptors involved in digestive tract movement functions, 5-HT receptor 1, 5-HT receptor 2, 5-HT receptor 3, 5-HT receptor 4, 5-HT receptor 7 and the like have been recognized. These receptors have been shown to be expressed in the nerve cells and smooth muscles of the gastrointestinal tract. The 5-HT released from EC cells controls digestive tract movement functions via the nerve cells and smooth muscles that express these 5-HT receptors. Hence, 5-HT is thought to be a kind of hormone that regulates gastrointestinal tract functions (non-patent document 1).

Although it has been known that when chemical stimulation or mechanical stimulation is given to EC cells, 5-HT release is promoted and gut movement is accentuated, little has been demonstrated about what is the molecular mechanism by which the above-described promotion of 5-HT release from EC cells is caused.

Currently, in the clinical settings for the field of digestive organ diseases, drugs that control the activity of 5-HT receptors are used. For example, 5-HT receptor 3 inhibitors are used to treat diarrhea type IBS, as antiemetics, and for other purposes, whereas 5-HT receptor 4 activators are used to treat constipation type IBS and digestive organ dysfunction and for other purposes. Because many IBS patients have an abnormality in postprandial blood 5-HT level, it has been demonstrated that 5-HT is associated with the pathologic condition. However, not many therapeutic drugs offer high satisfaction for patients with constipation type IBS or other digestive organ diseases (non-patent document 1).

TRPA1, belonging to the TRP (Transient Receptor Potential) channel family, was recently reported to be a temperature-sensitive channel, and TRPA1 was reported to become activated at temperatures of 17° C. or lower, and to become activated by nociceptive cold stimulation (non-patent document 2). It was also demonstrated that TRPA1 serves as a ligand agonizing ion channel that becomes activated not only by low temperatures, but also by stimulants such as mustard (non-patent document 3, patent document 1).

Furthermore, from experiments using TRPA1-deficient mice, it was demonstrated that TRPA1 activates primary afferent nociceptors to cause inflammatory algesia (non-patent document 4). From these experimental results, it is thought that TRPA1 plays an important part in the transmission mechanism by which an exogenous stimulant and an endogenous pain inducer cause inflammatory pain.

Although functions of TRPA1 concerning the sensory nerves and the like are already commonly known as described above, there is no research report on the roles of TRPA1 in the digestive tract, and its functions in the gut remain elusive.

[Patent document 1] WO2005/089206
[Non-patent document 1] TEXTBOOK of Gastroenterolorogy, Fourth Edition, ISBN 0-7817-2861-4
[Non-patent document 2] Cell, Vol. 112, 819-829(2003)
[Non-patent document 3] Nature, Vol. 427, 260-265(2004)
[Non-patent document 4] Cell, Vol. 124, 1269-1282(2006)

DISCLOSURE OF THE INVENTION

Problems to be Solved by the Invention

It is an object of the present invention to provide a screening tool and screening method for obtaining a substance useful as a prophylactic/therapeutic drug for diseases associated with 5-HT production/secretion abnormalities, including digestive organ diseases, and a means that can be used for the above-described screening, and to further provide a novel prophylactic/therapeutic drug for digestive organ diseases, and/or diseases associated with 5-HT production/secretion abnormalities, and the like.

Means of Solving the Problems

The present inventors found that TRPA1 is expressed in 5-HT releasing cells responsible for 5-HT production/secretion to regulate the 5-HT release from these cells, in more detail, the 5-HT release from such cells is specifically promoted by activation of TRPA1, and that the 5-HT release from such cells is specifically suppressed by inhibition of TRPA1. Based on these findings, the present inventors conceptualized that a substance capable of regulating the expression or channel activity of TRPA1 can be useful as a prophylactic and/or therapeutic drug for diseases associated with 5-HT production/secretion abnormalities (e.g., digestive organ diseases), and that a prophylactic and/or therapeutic drug for diseases associated with 5-HT production/secretion abnormalities can be obtained by screening for a substance capable of regulating the expression or channel activity of TRPA1, and developed the present invention.

Accordingly, the present invention provides the following:

[1] A screening method for a prophylactic and/or therapeutic drug for diseases associated with 5-HT production/secretion abnormalities, comprising evaluating a test substance to determine whether or not the test substance is capable of regulating the expression or channel activity of TRPA1.

[2] A screening method for a prophylactic and/or therapeutic drug for digestive organ diseases, comprising evaluating a test substance to determine whether or not the test substance is capable of regulating the expression or channel activity of TRPA1.

[3] The screening method according to [1] or [2] above, comprising the following steps (a) to (c):
(a) a step for bringing a test substance into contact with mammalian cells that are expressing TRPA1;
(b) a step for analyzing the expression or channel activity of TRPA1; and
(c) a step for selecting a substance capable of regulating the expression or channel activity of TRPA1.

[4] The screening method according to [3] above, wherein the mammalian cells that are expressing TRPA1 are chromaffin cells, pancreatic β cells or cells transformed with a TRPA1 expression vector.

[5] The screening method according to any one of [1] to [4] above, wherein the screening method is performed using a TRPA1 activator or a TRPA1 inhibitor.

[6] The screening method according to any one of [1] to [5] above, wherein the regulation of the expression or channel activity of TRPA1 is promotion of the expression or channel activity of TRPA1.

[7] The screening method according to any one of [1] to [5] above, wherein the regulation of the expression or channel activity of TRPA1 is suppression of the expression or channel activity of TRPA1.

[8] The screening method according to [3] above, which is a method of screening for a prophylactic or therapeutic drug for constipation type irritable bowel syndrome, functional dyspepsia or constipation by selecting a substance capable of promoting the expression or channel activity of TRPA1.

[9] The screening method according to [3] above, which is a method of screening for a prophylactic or therapeutic drug for diarrhea type irritable bowel syndrome, diarrhea or vomiting is by selecting a substance capable of suppressing the expression or channel activity of TRPA1.

[10] A screening tool for a prophylactic and/or therapeutic drug for diseases associated with 5-HT production/secretion abnormalities, comprising cells transformed with a TRPA1 expression vector.

[11] A screening tool for a prophylactic and/or therapeutic drug for a digestive organ disease, comprising cells transformed with a TRPA1 expression vector.

[12] The screening tool according to [11] above, wherein the digestive organ disease is irritable bowel syndrome, functional dyspepsia, constipation, diarrhea or vomiting.

[13] A prophylactic and/or therapeutic drug for diseases associated with 5-HT production/secretion abnormalities, comprising a substance capable of regulating the expression or channel activity of TRPA1.

[14] A prophylactic and/or therapeutic drug for a digestive organ disease, comprising a substance capable of regulating the expression or channel activity of TRPA1.

[15] A method of producing a prophylactic and/or therapeutic drug for diseases associated with 5-HT production/secretion abnormalities, comprising screening for a substance capable of regulating the expression or channel activity of TRPA1, and preparing the substance obtained by the screening as a pharmaceutical preparation.

[16] The production method according to [15] above, comprising the following steps (a) to (d):
(a) a step for bringing a test substance into contact with mammalian cells that are expressing TRPA1;
(b) a step for analyzing the expression or channel activity of TRPA1;
(c) a step for selecting a substance capable of regulating the expression or channel activity of TRPA1; and
(d) a step for preparing the substance obtained in the step (c) as a pharmaceutical preparation.

[17] A prophylactic and/or therapeutic drug for diseases associated with 5-HT production/secretion abnormalities, comprising a substance that can be obtained by the screening method according to [1] or [2] above.

[18] A prophylactic and/or therapeutic method for diseases associated with 5-HT production/secretion abnormalities, comprising administering a substance that can be obtained by the screening method according to [1] or [2] above to a patient in need of prevention and/or treatment.

[19] A use of a substance that can be obtained by the screening method according to [1] or [2] above, in producing a prophylactic and/or therapeutic drug for diseases associated with 5-HT production/secretion abnormalities.

[20] A screening method for a substance that exhibits a specified pharmacological effect, and that does not have the capability of regulating 5-HT release, comprising evaluating a test substance to determine whether or not the test substance that exhibits a specified pharmacological effect is capable of regulating the expression or channel activity of TRPA1.

[21] The screening method according to [20] above, comprising the following steps (a) to (c):
(a) a step for bringing a test substance that exhibits a specified pharmacological effect into contact with mammalian cells that are expressing TRPA1,
(b) a step for analyzing the expression or channel activity of TRPA1; and
(c) a step for selecting a substance that exhibits a specified pharmacological effect, and that does not regulate the expression or channel activity of TRPA1.

[22] A method of producing a pharmaceutical, comprising screening for a substance that exhibits a specified pharmacological effect, and that does not regulate the expression or channel activity of TRPA1, and preparing the substance obtained by the screening as a pharmaceutical preparation.

[23] A use of TRPA1 as a screening tool for a prophylactic and/or therapeutic drug for diseases associated with 5-HT production/secretion abnormalities.

[24] A use of TRPA1 as a screening tool for a prophylactic and/or therapeutic drug for a digestive organ disease.

Effect of the Invention

The screening tool and screening method of the present invention can be useful in, for example, developing a prophylactic and/or therapeutic drug for diseases associated with 5-HT production/secretion abnormalities, including digestive organ diseases, and a pharmaceutical that exhibits a specified pharmacological effect, and that is not desired to act as a result of the capability of regulating 5-HT release (e.g., adverse reactions in digestive organs).

The pharmaceutical of the present invention can be useful as, for example, a prophylactic and/or therapeutic drug for diseases associated with 5-HT production/secretion abnormalities, including digestive organ diseases, and as a pharmaceutical that exhibits a specified pharmacological effect, and that is not desired to act as a result of the capability of regulating 5-HT release. The present invention also provides a method of producing such a pharmaceutical.

BRIEF DESCRIPTION OF THE DRAWINGS

[FIG. 8-1] shows the results of a measurement of dog digestive tract movement by the strain gauge force transducer method. Allyl isothiocyanate accentuated stomach movement just after administration (solid arrow) and induced GMC (outlined arrow). The timing of administration is shown by the broken line.

[FIG. 8-2] shows the results of a measurement of dog digestive tract movement by the strain gauge force transducer method. The vehicle suppressed stomach movement just after administration (solid arrow), and did not induce GMC (outlined arrow). The timing of administration is shown by the broken line.

BEST MODE FOR CARRYING OUT THE INVENTION

1. Screening Tools

Figure 1:
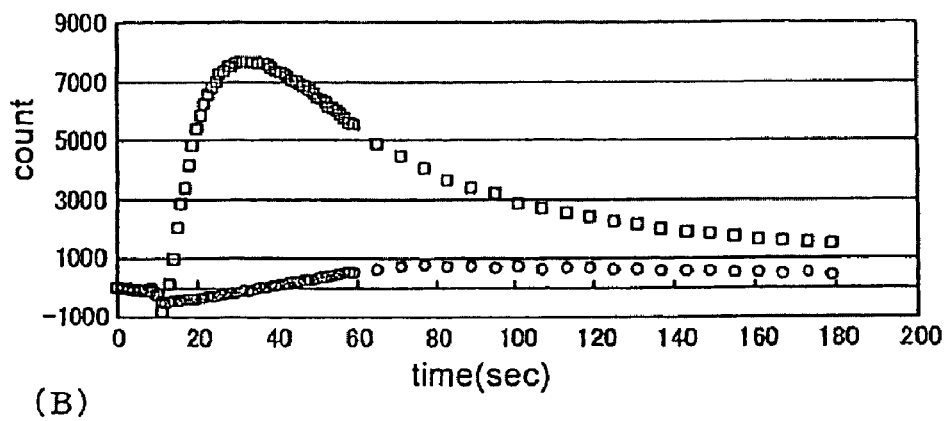
[FIG. 1] shows the results of an examination of changes in intracellular $Ca^{2+}$ concentration with the addition of 90 µM of each of allyl isothiocyanate (A), cinnamic aldehyde (B), and acrolein (C). The axis of ordinates indicates fluorescence intensity in terms of intracellular $Ca^{2+}$ concentration; the axis of abscissas indicates the time course after addition of each sample. □ shows the results for TRPA1-expressing CHO-K1 cells; ○ shows the results for control CHO-K1 cells.
Figure 1:
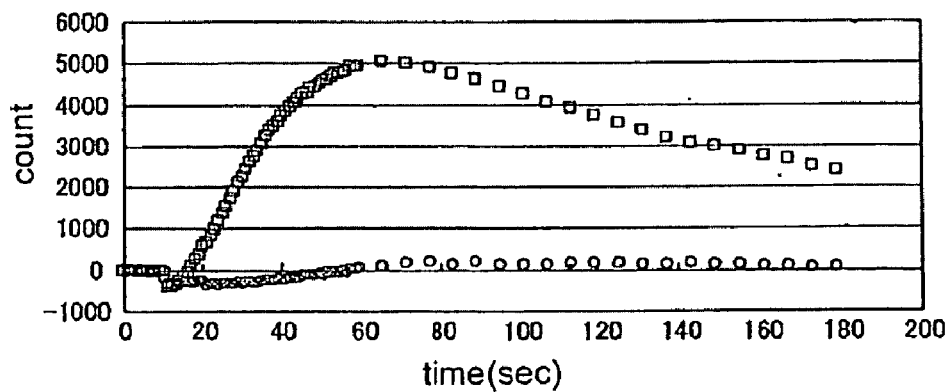
Figure 1:
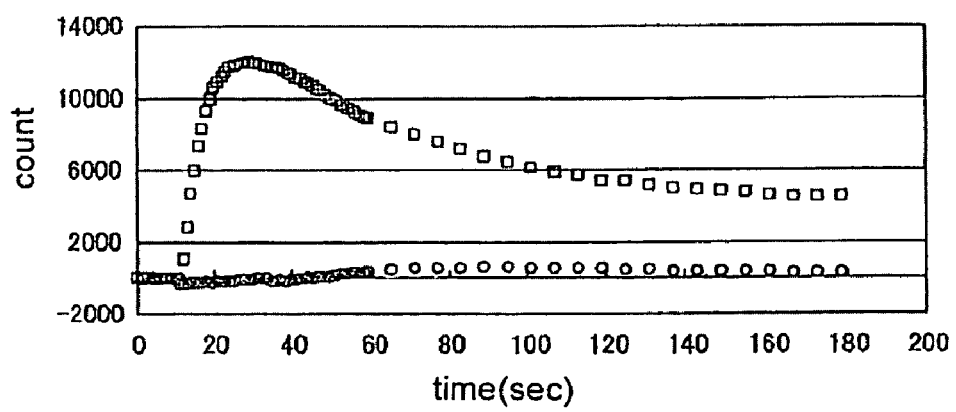

The present invention provides screening tools for a prophylactic and/or therapeutic drug for diseases associated with 5-HT production/secretion abnormalities, including digestive organ diseases. Examples of the screening tools of the present invention include polypeptide type screening tools and cell type screening tools.

(1) Polypeptide Type Screening Tool

Examples of polypeptides that can be used as the screening tool of the present invention include the following (i) to (iii):
(i) a polypeptide consisting of the same amino acid sequence as mammalian TRPA1;
(ii) (a) a polypeptide that comprises an amino acid sequence of mammalian TRPA1, and that becomes activated by a TRPA1 activator to exhibit cation-transmitting ion channel activity, or (b) a polypeptide that comprises an amino acid sequence of mammalian TRPA1 wherein 1 to 10 amino acids have been deleted, substituted, and/or inserted, and that becomes activated by a TRPA1 activator to exhibit cation transmitting ion channel activity [the tool polypeptide consisting of polypeptide (a) and the tool polypeptide consisting of polypeptide (b) are hereinafter together referred to as functionally equivalently modified tool polypeptides]; or
(iii) a polypeptide that consists of an amino acid sequence having an identity of 80% or more to an amino acid sequence of mammalian TRPA1, and that becomes activated by a TRPA1 activator to exhibit cation transmitting ion channel activity (hereinafter referred to as an identical tool polypeptide).

Hereinafter, these various polypeptides that can be used as the polypeptide type screening tool of the present invention are generically referred to as screening tool polypeptide or TRPA1 (polypeptide).

As used herein, "becomes activated by a TRPA1 activator to exhibit cation transmitting ion channel activity" means that when the current response value or calcium inflow or inflow of another cation for cells having a subject polypeptide expressed forcibly therein, or cells naturally expressing the same, stimulated with a TRPA1 activator, is compared with that for non-stimulated cells, the current response value or calcium inflow or inflow of the other cation for the stimulated cells is higher than the current response value or calcium inflow or inflow of the other cation for the non-stimulated cells. For example, a comparison of calcium inflow can be confirmed by the method described in Example 4, 5 or 13. Regarding the extent of the increase in calcium inflow, the P value is preferably not more than 0.05, and the P value is more preferably not more than 0.01, when a test is performed to determine the significant difference from the calcium inflow for non-stimulated cells.

The screening tool polypeptide of the present invention more preferably also exhibits cesium, sodium, and magnesium ion transmitting ion channel activity.

Examples of each polypeptide consisting of an amino acid sequence of mammalian TRPA1, which can be used as the polypeptide type screening tool of the present invention, include human-, mouse-, and rat-derived TRPA1 (e.g., SEQ ID NO:2, 4, and 6, respectively). TRPA1 has an amino acid sequence identity of 79.7% and a nucleotide identity of 80.7% between humans and mice, an amino acid sequence identity of 79.6% and a nucleotide identity of 79.9% between humans and rats, and an amino acid sequence identity of 96.6% and a nucleotide identity of 94.3% between mice and rats. In the present invention, human-derived TRPA1 (e.g., SEQ ID NO:2) is particularly preferred.

Although information on the amino acid sequence of TRPA1 and ligands that activate TRPA1 is available from various literature documents, none of them discloses or suggests the involvement in 5-HT release from EC cells or digestive tract movement.

Preferred as a functionally equivalently modified tool polypeptide that can be used as the polypeptide type screening tool of the present invention is (a) a polypeptide that consists of an amino acid sequence of mammalian TRPA1 wherein a total of 1 to 10 (more preferably 1 to 7, still more preferably 1 to 5, particularly preferably 1 or 2) amino acids have been deleted, substituted, inserted, and/or added at one or a plurality of sites, and that becomes activated by a TRPA1 activator to exhibit cation transmitting ion channel activity, is or (b) a polypeptide that comprises an amino acid sequence of mammalian TRPA1, and that becomes activated by a TRPA1 activator to exhibit cation transmitting ion channel activity.

Examples of a polypeptide that comprises an amino acid sequence of mammalian TRPA1, and that becomes activated by a TRPA1 activator to exhibit cation transmitting ion channel activity also include a polypeptide consisting of an amino acid sequence of mammalian TRPA1 wherein an appropriate marker sequence and the like have been added to the N terminus and/or C terminus thereof (that is, a fusion polypeptide), as far as it becomes activated by a TRPA1 activator to exhibit calcium ion transmitting ion channel activity.

As the aforementioned marker sequence, for example, a sequence for facilitating the confirmation of the expression, confirmation of the intracellular localization, or purification and the like of the polypeptide can be used; examples include FLAG epitope, hexa-histidine/tag, hemagglutinin/tag, or myc epitope and the like.

An identical tool polypeptide that can be used as the polypeptide type screening tool of the present invention has an identity of 80% or more, preferably 90% or more, more preferably 95% or more, still more preferably 98% or more, to an amino acid sequence of mammalian TRPA1, and one having an identity of 99% or more is particularly preferable. Herein, the degree of the aforementioned "identity" is determined by the ClustalV method using MegAlign (DNASTAR).

(2) Cell Type Screening Tool

Cells that can be used as the cell type screening tool of the present invention (hereinafter referred to as screening tool cells) are not particularly limited, as far as they express the aforementioned screening tool polypeptide when used as a cell type screening tool; they can be transformant cells forcibly expressing the aforementioned polypeptide by transformation with a foreign gene, or they can be natural cells expressing a screening tool polypeptide or a cell line thereof (e.g., RIN14B cells). Screening tool cells can also be provided in the form of a tissue containing the cells.

As screening tool cells that can be used as the cell type screening tool of the present invention, transformant cells incorporating the TRPA1 gene are preferred. Examples of such cells include the following (i) to (iii):
(i) transformant cells expressing a polypeptide consisting of an amino acid sequence of mammalian TRPA1;
(ii) transformant cells expressing a functionally equivalently modified tool polypeptide; or
(iii) transformant cells expressing an identical tool polypeptide.

Preferably, the mammalian cells expressing TRPA1 can be 5-HT releasing cells. As used herein, "5-HT releasing cells" refer to cells capable of releasing 5-HT through a mechanism of control mediated by TRPA1; examples include EC cells (e.g., EC cells derived from tissues such as gastrointestinal tract mucosa, lungs, skin, and pancreas) and endocrine cells such as pancreatic β cells. Such cells include normal cells and cancer cells.

The screening tools (1) and (2) above in the present invention can be useful in screening for a prophylactic and/or therapeutic drug for diseases associated with 5-HT production/secretion abnormalities, including digestive organ diseases. Such diseases include digestive organ diseases and non-digestive organ diseases. Examples of digestive organ diseases include irritable bowel syndrome (e.g., constipation type irritable bowel syndrome, diarrhea type irritable bowel is syndrome), functional dyspepsia, constipation, diarrhea, and vomiting. Examples of non-digestive organ diseases include eating disorders (e.g., bulimia, anorexia nervosa), pain, migraine, sleep disturbance (e.g., insomnia), mental disorders (e.g., depression, anxiety disorders, schizophrenia), blood coagulation disorders (e.g., platelet aggregation dysfunction, thrombosis, pulmonary thromboembolism), and carcinoid tumor.

Production of the screening tool of the present invention can be performed in accordance with a commonly known method (for example, Molecular Cloning-A Laboratory Manual, Cold Spring Harbor Laboratory, NY, 1989, WO02/052000, or WO02/053730).

The method of producing a polynucleotide that encodes the screening tool polypeptide of the present invention (hereinafter referred to as a screening tool polynucleotide) is not particularly limited; examples include (a) the method based on a polymerase chain reaction (PCR), (b) the method based on a conventional method of gene engineering technology (that is, a method wherein a transformant strain containing a desired cDNA is selected from among transformant strains resulting from transformation with a cDNA library), or (c) the chemical synthesis method and the like. These methods of production are hereinafter described in sequence.

In the PCR-based method [the aforementioned method of production (a)], for example, by the procedures shown below, the screening tool polynucleotide of the present invention can be produced.

That is, mRNA is extracted from cells (for example, human, mouse, or rat cells) or tissue having the capability of producing the screening tool polypeptide of the present invention. Next, on the basis of the base sequence of a polynucleotide that encodes the aforementioned polypeptide, a set of two primers between which full-length mRNA corresponding to the aforementioned polypeptide can be sandwiched, or a set of two primers between which the mRNA region of a portion thereof can be sandwiched, is prepared. By performing a reverse transcriptase-polymerase chain reaction (RT-PCR) while adjusting reaction conditions (for example, denaturation temperature or denaturant addition conditions and the like) as appropriate, a full-length cDNA that encodes the screening tool polypeptide of the present invention or a portion thereof can be obtained.

By performing PCR with a cDNA prepared from mRNA prepared from cells (for example, human, mouse, or rat cells) or tissue having the capability of producing the aforementioned polypeptide using a reverse transcriptase, or a commercially available cDNA derived from human, mouse, or rat cells or tissue, as the template, a full-length cDNA that encodes the aforementioned polypeptide or a portion thereof can also be obtained.

The thus-obtained full-length cDNA or portion thereof may be integrated into an appropriate expression vector and expressed in host cells, whereby the aforementioned polypeptide can be produced.

In the method based on a conventional method of gene engineering technology [the aforementioned method of production (b)], for example, the screening tool polynucleotide of the present invention can be produced per the procedures shown below.

First, with mRNA prepared by the aforementioned PCR-based method as the template, using a reverse transcriptase, a single-stranded cDNA is synthesized, after which a double-stranded cDNA is synthesized from this single-stranded cDNA.

Next, a recombination plasmid harboring the aforementioned double-stranded cDNA is prepared, after which it is introduced to Escherichia coli (for example, DH5α strain, HB101 strain, or JM109 strain) to transform the strain, and a recombinant is selected with, for example, drug resistance to tetracycline, ampicillin, or kanamycin as the index. When the host cell is *Escherichia coli*, transformation of the host cell can be performed by Hanahan's method (Hanahan, D. J., Mol. Biol., 166, 557-580, 1983). Commercially available competent cells can also be used. In addition to plasmids, phage vectors such as the lambda series can also be used as vectors.

As a method of selecting a transformant strain having a desired cDNA from among the transformant strains thus obtained, for example, (1) a screening method based on hybridization using a synthetic oligonucleotide probe, or (2) a screening method based on hybridization using a PCR-prepared probe can be adopted.

A method of collecting the screening tool polynucleotide of the present invention from the desired transformant strain obtained can be performed in accordance with a commonly known method. For example, this method can be performed by separating a fraction corresponding to the plasmid DNA from the cells, and cleaving out the cDNA region from the plasmid DNA obtained.

In the method based on chemical synthesis [the aforementioned method of production (c)], by, for example, binding a DNA fragment produced by chemical synthesis, the screening tool polynucleotide of the present invention can be produced. Each DNA can be synthesized using a DNA synthesizer [for example, Oligo 1000M DNA Synthesizer (produced by Beckman), or 394 DNA/RNA Synthesizer (produced by Applied Biosystems) and the like].

Sequencing of the DNAs obtained by the various methods described above can be performed by, for example, the Maxam-Gilbert method of chemical modification (Maxam, A. M. and Gilbert, W., Methods in Enzymology, 65, 499-559, 1980), the dideoxynucleotide chain termination method (Messing, J. and Vieira, J., Gene, 19, 269-276, 1982) and the like.

By again integrating the isolated screening tool polynucleotide of the present invention into an appropriate vector to transform host cells (including eukaryotic host cells and prokaryotic host cells), the cells or screening tool cells of the present invention can be obtained. It is also possible to express the polynucleotide in the respective host cells by introducing an appropriate promoter and a sequence involved in the character expression into these vectors.

For example, eukaryotic host cells include cells of vertebral animals, insects, yeast and the like; examples of vertebral animal cells include COS cells, which are monkey cells (Gluzman, Y., Cell, 23, 175-182, 1981), the dihydrofolate reductase-deficient line of Chinese hamster ovarian cells (CHO) (Urlaub, G. and Chasin, L. A., Proc. Natl. Acad. Sci. USA, 77, 4216-4220, 1980), fetal human kidney-derived HEK293 cells, 293-EBNA cells (Invitrogen) prepared by introducing the Epstein-Barr virus EBNA-1 gene to the aforementioned HEK293 cells, and the like.

As an expression vector for vertebral animal cells, one having a promoter lying upstream of the polynucleotide to be expressed, an RNA splicing site, a polyadenylation site, and a transcription termination sequence and the like can usually be used, and can have a replication origin as required. Examples of the aforementioned expression vector include, for example, pSV2dhfr, which has the early promoter of SV40 (Subramani, S. et al., Mol. Cell. Biol., 1, 854-864, 1981), pEF-BOS, which has a human elongation factor promoter (Mizushima, S. and Nagata, S., Nucleic Acids Res., 18, 5322, 1990), or pCEP4, which has a cytomegalovirus promoter (Invitrogen), and the like.

When COS cells are used as the host cells, an expression vector that has an SV40 replication origin, that is capable of self-proliferating in the COS cells, and that is further provided with a transcription promoter, a transcription termination signal, and an RNA splicing site, can be used; examples include pME18S (Maruyama, K. and Takebe, Y., Med. Immunol., 20, 27-32, 1990), pEF-BOS (Mizushima, S. and Nagata, S., Nucleic Acids Res., 18, 5322, 1990), or pCDM8 (Seed, B., Nature, 329, 840-842, 1987) and the like.

The aforementioned expression vector can be incorporated into COS cells by, for example, the DEAE-dextran method (Luthman, H. and Magnusson, G., Nucleic Acids Res., 11, 1295-1308, 1983), the calcium phosphate-DNA co-precipitation method (Graham, F. L. and van der Ed, A. J., Virology, 52, 456-457, 1973), a method using a commercially available transfection reagent (for example, FuGENE™ 6 Transfection Reagent; produced by Roche Diagnostics), or electroporation (Neumann, E. et al., EMBO J., 1, 841-845, 1982) and the like.

When CHO cells are used as the host cells, transformant cells that stably produce the screening tool polypeptide of the present invention can be obtained by co-transfecting an expression vector harboring a polynucleotide for the screening tool of the present invention with a vector capable of expressing the neo gene, which functions as a G418 resistance marker, for example, pRSVneo (Sambrook, J. et al. Molecular Cloning-A Laboratory Manual, Cold Spring Harbor Laboratory, NY, 1989) or pSV2-neo (Southern, P. J. and Berg, P., J. Mol. Appl. Genet., 1, 327-341, 1982) and the like, and selecting a G418-resistant colony.

When 293-EBNA cells are used as the host cells, pCEP4 (Invitrogen), which has the replication origin of Epstein-Barr virus, and which is capable of self-replication in 293-EBNA cells, and the like can be used as the expression vectors.

The transformants can be cultured in accordance with a conventional method; by the aforementioned cultivation, the screening tool polypeptide of the present invention is produced through the cell membrane. As media that can be used for the aforementioned cultivation, various media in common use can be selected as appropriate according to the host cells adopted. For example, in the case of COS cells, for example, a medium prepared by adding as required a serum component such as fetal bovine serum (FBS) to a medium such as RPMI-1640 medium or Dulbecco's modified Eagle medium (DMEM) can be used. In the case of 293-EBNA cells, a medium prepared by adding G418 to a medium such as Dulbecco's modified Eagle medium (DMEM) supplemented with a serum component such as fetal bovine serum (FBS) can be used.

The screening tool polypeptide of the present invention, produced by culturing the transformant, can be separated and purified by various commonly known methods of separation based on a physical property, biochemical property or the like of the aforementioned polypeptide. Specifically, cells or a cell membrane fraction containing the aforementioned polypeptide can be subjected to, for example, treatment with an ordinary protein precipitant, ultrafiltration, various liquid chromatographies [for example, molecular sieve chromatography (gel filtration), adsorption chromatography, ion exchange chromatography, affinity chromatography, or high performance liquid chromatography (HPLC) and the like], or dialysis, or a combination thereof and the like, to purify the aforementioned polypeptide.

By fusing the screening tool polypeptide of the present invention with a marker sequence in frame, confirmation of the expression or purification and the like of the aforementioned polypeptide is facilitated. Examples of the aforementioned marker sequence include FLAG epitope, hexa-histidine/tag, hemagglutinin/tag, or myc epitope and the like. By inserting a specific amino acid sequence recognized by a protease (for example, enterokinase, factor Xa, or thrombin and the like) between the marker sequence and the aforementioned polypeptide, it is possible to cleave out the marker sequence portion with these proteases.

2. Screening Methods

The present invention provides screening methods comprising evaluating a test substance to determine whether or not the test substance is capable of regulating the expression or channel activity of TRPA1.

The screening methods of the present invention can be roughly divided into a screening method for a prophylactic and/or therapeutic drug for diseases associated with 5-HT production/secretion abnormalities, including digestive organ diseases, comprising selecting a substance capable of regulating the expression or channel activity of TRPA1 (screening method I), and a screening method for a substance not having the capability of regulating 5-HT release, comprising selecting a substance that does not regulate the expression or channel activity of TRPA1 (screening method II).

Hereinafter, the individual screening methods are described in detail.

2.1. Screening Method Comprising Selecting a Substance Capable of Regulating the Expression or Channel Activity of TRPA1

The present invention provides a screening method comprising evaluating a test substance to determine whether or not the test substance is capable of regulating the expression or channel activity of TRPA1, and selecting a substance capable of regulating the expression or channel activity of TRPA1 (screening method I).

The test substance subjected to the screening method I is not particularly limited; for example, various commonly known compounds (including peptides) registered with chemical files, a set of compounds obtained by combinatorial chemistry technology (Terrett, N. K. et al. Tetrahedron, 51, 8135-8137, 1995), or a set of random peptides prepared by applying the phage display method (Felici, F. et al., J. Mol. Biol., 222, 301-310, 1991) and the like can be used. Natural components derived from microorganisms, plants, marine organisms or animals (for example, culture supernatant or tissue extract) and the like can also be used as test substances for screening. Furthermore, compounds (including peptides) selected by the screening method of the present invention, for example, compounds (including peptides) prepared by chemically or biologically modifying allyl isothiocyanate, cinnamic aldehyde, or acrolein, can be used.

In detail, the screening method I of the present invention comprises the following steps (a) to (c):

(a) a step for bringing a test substance into contact with the screening tool of the present invention (e.g., screening tool cells);
(b) a step for analyzing (measuring, detecting) the expression or channel activity of TRPA1; and
(c) a step for selecting a substance capable of promoting or suppressing the expression or channel activity of TRPA1.

The expression of TRPA1 can be analyzed by, for example, using the method described below in mammalian cells expressing TRPA1 (that is, screening tool cells).

The expression of TRPA1 can also be analyzed using cells that allow a reporter assay for a TRPA1 transcription regulatory region. The cells that allow an reporter assay for the TRPA1 transcription regulatory region can be cells transformed with an expression vector harboring a TRPA1 transcription regulatory region and a reporter gene functionally joined to the region. The TRPA1 transcription regulatory region is not particularly limited, as far as it is a region capable of controlling the expression of TRPA1; examples include a region up to about 2 kbp upstream of the transcription initiation point, or a region that consists of the base sequence of the region wherein one or more bases have been deleted, substituted or added, and that has the capability of controlling the transcription of a target gene and the like. Examples of reporter genes include the GFP (green fluorescent protein) gene, the GUS (β-glucuronidase) gene, the LUC (luciferase) gene, the CAT (chloramphenicol acetyltransferase) gene and the like.

As used herein, "a substance that promotes the activity of the channel" has the same definition as that for "a substance that activates the channel" to refer to a substance that activates the ion channel by being brought into contact with a test substance, including both a substance that directly activates the channel, like TRPA1 activators, and a substance that promotes the activation of a substance that directly activates the channel. By performing the above-described step in the presence of a TRPA1 activator, a substance that promotes the activation of TRPA1 by a TRPA1 activator can be screened for; a screening method for a substance that promotes the activation of the aforementioned polypeptide by a TRPA1 activator is also included in the above-described screening method. Examples of the TRPA1 activator include allyl isothiocyanate, cinnamic aldehyde, and acrolein.

As used herein, "a substance that suppresses the activity of the channel" has the same definition as that for "a substance that inhibits the channel" to refer to a substance that suppresses the activation of the ion channel by being brought into contact with a test substance, including both a substance that inhibits channel activity, like a TRPA1 inhibitor, and a substance that increases the activity of a substance that directly inhibits the channel. By performing the above-described step in the presence of a TRPA1 inhibitor, a substance that promotes the inactivation of TRPA1 by a TRPA1 inhibitor can be screened for; a screening method for a substance that increases the inactivation of the aforementioned polypeptide by a TRPA1 inhibitor is also included in the above-described screening method. Examples of the TRPA1 inhibitor include Ruthenium Red.

Analysis of channel activity in the screening method of the present invention can be performed in a variety of modes. Examples of such modes include (a) utilization of the patch-clamp method, (b) utilization of radioisotope ion inflow, (c) utilization of an intracellular $Ca^{2+}$ detection dye. The individual screening methods are hereinafter described.

When screening is performed by utilizing the patch-clamp method of (a), by, for example, analyzing (preferably measuring) the whole cell current in cells using the whole cell patch-clamp method (Hille, B., Ionic Channels of Excitable Membranes, 2nd Ed., 1992, Sinauer Associates Inc., MA), an analysis can be performed to determine whether or not the channel is activated.

More specifically, the screening tool cells of the present invention are subjected to membrane potential fixation by the whole cell patch-clamp method, and the whole cell current of the aforementioned cells is measured. In this case, as the extracellular fluid, a solution containing 149 mmol/L-NaCl, 5 mmol/L-KCl, 2 mmol/L-$CaCl_2$, 0.8 mmol/L-$MgCl_2$, and 10 mmol/L-HEPES-Na (pH 7.4) can be used, and as the intracellular fluid, a solution comprising 147 mmol/L-CsCl, 4.5 mmol/L-EGTA, and 9 mmol/L-HEPES-K (pH 7.2) and the like can be used. Subsequently, by measuring changes in current with the addition of a test substance to the extracellular fluid or intracellular fluid, a substance that activates the channel of the polypeptide or screening tool polypeptide of the present invention can be screened for. For example, if the changes in whole cell current upon stimulation by activation of the aforementioned channel intensify with the addition of a test substance, the aforementioned test substance can be judged to be a substance that activates the aforementioned channel. As a substance that activates the channel, it is preferable to select, for example, one that produces changes in cell current to the same extent as a TRPA1 activator as described in an Example.

When screening is performed by utilizing a radioisotope ion inflow of (b), channel activity can be analyzed (preferably measured) with various radioisotopes of $Ca^{2+}$ ions as indexes [Sidney P. Colowick and Nathan O. Kaplan, Methods in ENZYMOLOGY, 88(1), 1982, Academic Press, 346-347]. This analytical procedure is based on the finding that the screening tool polypeptide of the present invention transmits $Ca^{2+}$ ions.

In the screening tool cells of the present invention, by analyzing the amount of the radioactivity flowing into the aforementioned cells, or the radioactivity remaining outside the cells, using a test substance, whether or not the channel of the screening tool polypeptide of the present invention is activated can be determined.

Specifically, the amount of the radioactivity can be measured using, for example, $^{45}Ca^{2+}$, a radioisotope of $Ca^{2+}$ ion. If a test substance activates the aforementioned channel in a state wherein $^{45}Ca^{2+}$ is in the reaction liquid, the radioisotope flows into the cells; therefore, the radioactivity in the extracellular fluid (that is, radioactivity remaining in the extracellular fluid), or the radioactivity of the radioisotope flowing into the cells, can be used as the index of channel activation (Toshio Kuroki, Huh, Nam-Ho, and Kazuhiro Chida edts., Jikken Igaku, extra issue, "Bunshi Seibutsugaku Kenkyu No Tameno Baiyou Saibou Jikkenhou", 1995, Yodosha Co., Ltd.). As a substance that activates the channel, for example, one that allows $Ca^{2+}$ to flow into cells to the same extent as a TRPA1 activator as described in an Example, specifically, one that has an $EC_{50}$ of 100 µmol/L or less, is preferably selected.

When screening is performed by utilizing an intracellular $Ca^{2+}$ detection dye of (c), for example, Fluo3-AM and the like can be used as an intracellular $Ca^{2+}$ detection dye. The intracellular $Ca^{2+}$ detection dye makes it possible to optically analyze (preferably measure) changes in intracellular $Ca^{2+}$ concentration resulting from the opening of the ion channel of the screening tool polypeptide of the present invention (Yoshihisa Kudo edt., Jikken Igaku, extra issue, "Saibounai Karushiumu Jikken Purotokoru", 1996, Yodosha Co., Ltd.). By using these dyes, the activity of the aforementioned channel can be measured. If the intracellular $Ca^{2+}$ detection dye shows a change in the presence of a test substance compared to the finding obtained in the absence of the test substance, in the aforementioned channel expression cells, the test substance can be judged to be a substance that activates the aforementioned channel. This method is not particularly limited; for example, by allowing the screening tool cells of the present invention to incorporate an intracellular $Ca^{2+}$ detection dye, and then optically measuring quantitative changes in the intracellular $Ca^{2+}$ detection dye caused by the test substance in the aforementioned cells, whether or not the aforementioned channel is activated can be determined.

More specifically, if the amount of $Ca^{2+}$ flowing into cells increases with the addition of a test substance compared to the amount obtained in the absence of the test substance, the aforementioned test substance can be judged to be a substance that activates the channel. This method is preferably performed under the conditions described in Examples 3, 4, 5, and 13; as a substance that activates the channel, for example, one that promotes quantitative changes in intracellular $Ca^{2+}$ detection dye to the same extent as that caused by a TRPA1 activator as described in an Example, one having an $EC_{50}$ of 100 µmol/L or less under the conditions of Example 4, is preferably selected. As a substance that inactivates the channel, for example, one that promotes quantitative changes in intracellular $Ca^{2+}$ detection dye to the same extent as that caused by a TRPA1 inhibitor as described in an Example, specifically, one having an $EC_{50}$ of 100 µmol/L or less under the conditions of Example 5, is preferably selected.

In the aforementioned screening method (a), (b), or (c), out of compounds that do not directly activate the aforementioned channel, one that exhibits a higher activity than that obtained without administration of the aforementioned test substance when a TRPA1 activator at a is concentration that does not 100% activate the aforementioned channel, for example, a TRPA1 activator at 1 µmol/L, is administered after administration of the aforementioned test substance, can be judged to promote the activity of the aforementioned channel. As stated above, by performing the above-described screening in the presence of a TRPA1 activator, a compound that promotes the activation of the screening tool polypeptide of the present invention by the TRPA1 activator can be screened for. As a substance that promotes the activation, one that significantly promotes the activity of the TRPA1 activator, specifically, one having an $EC_{50}$ of 100 µmol/L or less, is preferably selected.

For inhibitor screening methods as well, in the aforementioned screening method (a), (b), or (c), out of compounds that do not directly inactivate the aforementioned channel, one that exhibits a higher inhibitory activity than that obtained without administration of the aforementioned test substance when a TRPA1 inhibitor at a concentration that does not completely inactivate the aforementioned channel, for example, a TRPA1 inhibitor at 100 nmol/L, is administered after administration of the aforementioned test substance, can be judged to inactivate the activity of the channel. As stated above, by performing the above-described screening in the presence of a TRPA1 inhibitor, a compound that increases the inactivation of the screening tool polypeptide of the present invention by the TRPA1 inhibitor can be screened for. As a substance that promotes the inactivation, one that significantly promotes the inhibitory activity of the TRPA1 inhibitor, specifically, one having an $EC_{50}$ of 100 µmol/L or less, is preferably selected.

When a screening polypeptide that exhibits cesium, sodium, or magnesium ion transmitting ion channel activity is used, a radioisotope of cesium, sodium, or magnesium can be used as is the indicator in place of $Ca^{2+}$ as in (b). Specifically, the screening can be performed with reference to the method described in Sidney P. Colowick and Nathan O. Kaplan, Methods in ENZYMOLOGY, 88(1), 1982, Academic Press, 346-347. This analytical procedure is based on the finding that the screening polypeptide of the present invention transmits cesium ions, sodium ions, and magnesium ions.

The screening method I of the present invention can be useful in developing a prophylactic and/or therapeutic drug for diseases associated with 5-HT production/secretion abnormalities, including digestive organ diseases, as described above. For example, a substance capable of promoting the expression or channel activity of TRPA1 can be useful as a prophylactic or therapeutic drug for constipation type irritable bowel syndrome, functional dyspepsia or constipation among digestive organ diseases, and also as a prophylactic/therapeutic drug for bulimia, insomnia, depression, anxiety disorders, migraine, and platelet aggregation dysfunction among non-digestive organ diseases. On the other hand, a substance capable of suppressing the expression or channel activity of TRPA1 can be useful as, for example, a prophylactic or therapeutic drug for diarrhea type irritable bowel syndrome, diarrhea or vomiting among digestive organ diseases, and also as a prophylactic/therapeutic drug for anorexia nervosa, pain, schizophrenia, carcinoid tumor, thrombosis, and pulmonary thromboembolism among non-digestive organ diseases.

As the screening method I of the present invention, a screening method comprising selecting a substance that binds to TRPA1, comprising the following steps (a) to (c), can also be mentioned:
(a) a step for bringing a test substance into contact with the polypeptide type screening tool of the present invention;
(b) a step for analyzing the binding of the aforementioned test substance to the aforementioned screening tool; and
(c) a step for selecting a substance that binds to the aforementioned screening tool.

The screening method I of the present invention, in addition to the aforementioned steps (a) to (c), may further comprise as the step (d) a step for determining whether or not the selected substance is effective as a prophylactic and/or therapeutic drug for diseases associated with 5-HT production/secretion abnormalities, or a step for determining whether or not the selected substance is effective as a prophylactic and/or therapeutic drug for digestive tract diseases. This confirmatory step can be performed by using a method obvious to those skilled in the art, or a method improved therefrom. Examples include a test to measure gut movement using animals, measurement of the amount of defecation, measurement of fecal nature, measurement of contraction using an isolated gut, measurement of the amount of gut water secretion and the like as described in Examples 19 to 22 below.

2.2. Screening Method Comprising Selecting a Substance that Does Not Regulate the Expression or Channel Activity of TRPA1

The present invention provides a screening method comprising evaluating a test substance to determine whether or not the test substance is capable of regulating the expression or channel activity of TRPA1, and selecting a substance that does not regulate the expression or channel activity of TRPA1 (screening method II).

The test substance subjected to the screening method II is not particularly limited, as far as it exhibits a specified pharmacological effect (e.g., drugs, bioactive substances); for example, the above-described test substances can be used. An analysis of the expression or channel activity of TRPA1 in the screening method II of the present invention can be performed in the same manner as the screening method I. The screening method II of the present invention can be useful in developing a pharmaceutical that exhibits a specified pharmacological effect, and that is not desired to act as a result of the capability of regulating 5-HT release (e.g., adverse reactions in digestive organs) (e.g., pharmaceuticals with a decreased incidence of adverse reactions).

3. Pharmaceutical

The present invention provides a pharmaceutical composition containing a substance capable of regulating the expression or channel activity of the screening tool polypeptide of the present invention, for example, a prophylactic and/or therapeutic drug for diseases associated with 5-HT production/secretion abnormalities, including digestive organ diseases.

The present invention also provides a prophylactic and/or therapeutic method for diseases associated with 5-HT production/secretion abnormalities, including digestive organ disease, comprising administering a substance capable of regulating the expression or channel activity of a screening tool polypeptide, and a use of a substance capable of regulating the expression or channel activity of the screening tool polypeptide of the present invention for producing a pharmaceutical composition.

The present invention further provides a method of producing a pharmaceutical composition, comprising evaluating a test substance to determine whether or not the test substance is capable of regulating the expression or channel activity of TRPA1, and preparing the evaluated substance as a pharmaceutical preparation, and a pharmaceutical composition is obtained by the method of production.

In an embodiment, the method of production of the present invention can be a method of producing a prophylactic and/or therapeutic drug for diseases associated with 5-HT production/secretion abnormalities, including digestive organ diseases, comprising screening for a substance capable of regulating the expression or channel activity of TRPA1, and preparing the substance obtained by the screening as a pharmaceutical preparation (method of production I).

In more detail, the method of production I of the present invention can comprise the following steps (a) to (d):
(a) a step for bringing a test substance into contact with the screening tool of the present invention;
(b) a step for analyzing the expression or channel activity of TRPA1; and
(c) a step for selecting a substance capable of regulating the expression or channel activity of TRPA1;
(d) a step for preparing the substance obtained in the step (c) as a pharmaceutical preparation.

In another embodiment, the method of production of the present invention can be a method of producing a pharmaceutical composition, comprising screening for a substance that exhibits a specified pharmacological effect, and that does not regulate the expression or channel activity of TRPA1, and preparing the substance obtained by the screening as a pharmaceutical preparation (method of production II).

In more detail, the method of production II of the present invention can comprise the following steps (a) to (d):
(a) a step for bringing a test substance that exhibits a specified pharmacological effect into contact with the screening tool of the present invention;
(b) a step for analyzing the expression or channel activity of TRPA1 and
(c) a step for selecting a substance that does not regulate the expression or channel activity of TRPA1, and that exhibits a specified pharmacological effect;
(d) a step for preparing the substance obtained in the step (c) as a pharmaceutical preparation.

The steps (a) to (c) in the method of production I and method of production II of the present invention can be performed in the same manner as the screening method of the present invention.

A substance selected through the above-described steps (a) to (c) in the method of production of the present invention [for example, DNAs, proteins (including antibodies or antibody fragments), peptides, or other compounds] can be prepared as a pharmaceutical preparation using a pharmacologically acceptable carrier, excipient, and/or other additives in common use in the art chosen according to the kind thereof, as a pharmaceutical composition.

Examples of modes of administration include oral administration of tablets, pills, capsules, granules, fine granules, powders, or solutions for oral administration and the like, or parenteral administration of injections such as intravenous injection or intramuscular injection, suppositories, transdermal preparations, or per-mucosal preparations and the like. In particular, for peptides that are digested in the stomach, parenteral administration by intravenous injection and the like is preferred.

In the solid composition for oral administration, one or more active substances and at least one inactive diluent, for example, lactose, mannitol, glucose, microcrystalline cellulose, hydroxypropylcellulose, starch, polyvinylpyrrolidone, or magnesium metasilicate aluminate and the like can be blended. The aforementioned composition can contain, in accordance with a conventional method, an additive other than an inactive diluent, for example, a lubricant, a disintegrant, a stabilizer, or a solvent or solubilizer and the like. Tablets or pills can be coated with a sugar coating or a film such as of a substance that dissolves in the stomach or intestine as required.

The liquid composition for oral administration can contain, for example, an emulsion, a solution, a suspension, a syrup, or an elixir, and can contain an inactive diluent in general use, for example, purified water or ethanol. The aforementioned composition can contain an additive other than an inactive diluent, for example, a wetting agent, a suspending agent, a sweetening agent, a flavoring agents, or an antiseptic.

Injections for parenteral administration can contain a sterile, aqueous or non-aqueous solution, suspension, or emulsion. The aqueous solution or suspension can contain, for example, distilled water for injection or physiological saline and the like as a diluent. As examples of the diluent for the non-aqueous solution or suspension, propylene glycol, polyethylene glycol, vegetable oils (for example, olive oil), alcohols (for example, ethanol), or polysorbate 80 and the like can be contained. The aforementioned composition can further contain a wetting agent, an emulsifier, a dispersing agent, a stabilizer, a solvent or a solubilizer, or an antiseptic and the like. The aforementioned composition can be sterilized by, for example, filtration through a bacterial retention filter, formulation of an antibacterial agent, or irradiation. It is also possible to produce a sterile solid composition and dissolve it in sterile water or another medium for sterile injection before use.

The dose can be determined as appropriate in consideration of the potency of the activity of an active ingredient, symptoms, subject age or sex and the like.

For example, in the case of oral administration, the dose is normally about 0.1 to 100 mg, preferably 0.1 to 50 mg, per day for an adult (assuming a body weight of 60 kg). In the case of parenteral administration, in the form of an injection, the dose is 0.01 to 50 mg, preferably 0.01 to 10 mg, per day.

EXAMPLES

The present invention is hereinafter described in further detail by means of the following examples, which, however, do not limit the scope of the present invention.

Example 1

Isolation of Human-derived TRPA1 and Construction of Expression Vector

After 10 ng of human brain mRNA (Clontech) was treated with DNase, reverse transcription was performed using a kit for reverse transcription-polymerase chain reaction (RT-PCR) (SUPERSCRIPT First-Strand Synthesis System for RT-PCR; Invitrogen) to synthesize a first strand cDNA. With this first strand cDNA as the template, using Taq DNA polymerase (LA Taq DNA polymerase; Takara Shuzo), PCR was performed by the Hot Start method. The aforementioned PCR was performed using oligonucleotides consisting of the base sequences shown by SEQ ID NO:7 as a sense primer, and SEQ ID NO:8 as an antisense primer; first, thermal denaturation was performed at 98° C. (1 minute), after which a cycle consisting of heat treatment at 98° C. (15 seconds)/56° C. (30 seconds)/72° C. (5 minutes) was repeated 35 times. As a result, an about 3.3-kbp DNA fragment was amplified.

This DNA fragment was cloned into the pCR-TOPO vector using a cloning kit (TOPO XL PCR Cloning Kit; Invitrogen). The plasmid DNA obtained was digested with the restriction endonucleases KpnI and HindIII, after which it was cloned using the plasmid pcDNA3.1(+) (Invitrogen). The aforementioned plasmid pcDNA3.1(+) has a cytomegalovirus-derived promoter sequence, and can be used to express a protein in animal cells.

When the base sequence of the clone obtained was analyzed by the dideoxy terminator method using a DNA sequencer (ABI3700 DNA Sequencer; Applied Biosystems), the base sequence shown by SEQ ID NO:1 was obtained. When these sequences were translated into amino acid sequences, the amino acid sequence shown by SEQ ID NO:2 was obtained.

Example 2

Expression of Protein in Animal Cells

To detect the TRPA1 channel activity of a polypeptide consisting of the amino acid sequence shown by SEQ ID NO:2, the expression vector obtained in Example 1 above was transfected to animal cells, whereby the aforementioned protein was expressed. Fetal human kidney-derived HEK293 cells and CHO-K1 cells were transformed using the expression vector obtained in Example 1 and a transformation reagent (LIPOFECTAMINE or LIPOFECTAMINE2000; Invitrogen) to induce the expression of the polypeptide consisting of the amino acid sequence shown by SEQ ID NO:2.

The aforementioned operation was performed per the protocol attached to the aforementioned transformation reagent, and a commonly known method (Toshio Kuroki, Huh, Nam-Ho, and Kazuhiro Chida edts., Jikken Igaku, extra issue, "Bunshi Seibutsugaku Kenkyu No Tameno Baiyou Saibou Jikkenhou", 1995, Yodosha Co., Ltd.).

Example 3

Measurement of Intracellular Calcium Concentrations by FLIPR

Various test samples were added to CHO-K1 cells forced to is transiently express TRPA1 by the transfection operation of Example 2 above, and the resulting changes in intracellular calcium concentration were measured using FLIPR (Molecular Device).

To measure the changes in intracellular calcium concentration by FLIPR, the following pre-treatment was performed. First, an assay buffer for adding the fluorescent dye Fluo3-AM (DOJIN) to the cells, or for washing the cells just before performing the FLIPR assay, was prepared. To a solution prepared by adding 20 ml of 1M HEPES (pH 7.4) (Invitrogen) to 1000 ml of HBSS (Invitrogen) (hereinafter, HBSS/HEPES solution), 10 ml of a solution prepared by dissolving 710 mg of probenecid (Sigma) in 5 ml of 1N NaOH and then adding 5 ml of the HBSS/HEPES solution, was added and mixed, and this solution was used as the assay buffer. Next, 50 µg of Fluo3-AM was dissolved in 22 µl of DMSO (DOJIN), and an equal volume of 20% pluronic acid (Molecular Probes) was added and mixed, after which this mixture was added to 10.6 ml of the assay buffer supplemented with 105 µl of fetal bovine serum, whereby a fluorescent dye solution was prepared. The medium for the transfection-treated CHO-K1 cells was removed, and the fluorescent dye solution was immediately dispensed at 100 μl per well, after which the cells were cultured in a $CO_2$ incubator for 1 hour to allow the cells to incorporate the fluorescent dye. After the cultivation, the cells were washed with the above-described assay buffer, and then set to the FLIPR. A test sample for addition to the TRPA1-expressing CHO-K1 cells was prepared using the assay buffer, and simultaneously set to the FLIPR. After this pretreatment was performed, changes in intracellular calcium concentration after addition of the various test samples were measured with the FLIPR.

As a result, it was found that when allyl isothiocyanate (Wako Pure Chemical Industries), cinnamic aldehyde (Wako Pure Chemical Industries), acrolein (Sigma) and the like were added, CHO-K1 cells expressing human TRPA1 responded specifically (elevation of intracellular calcium concentration). On the other hand, in an investigation using CHO-K1 cells not expressing the polypeptide shown by SEQ ID NO:2 (negative control cells), none of these compounds produced an elevation of fluorescence intensity. Hence, it was confirmed that allyl isothiocyanate, cinnamic aldehyde, and acrolein are activators of human TRPA1 (FIG. 1).

Example 4

Screening for TRPA1 Activators

Compounds that activate a polypeptide consisting of the amino acid sequence shown by SEQ ID NO:2 (activators) were screened for. As an index of activation, calcium inflow in the cells was detected using a calcium-sensitive fluorescent reagent; specifically, the method described in Example 3 was used. As the screening criterion, compounds having an $EC_{50}$ of 100 μmol/L or less were selected.

As a result of investigations of various compounds, an elevation of fluorescence intensity was detected with allyl isothiocyanate, cinnamic aldehyde, and acrolein. The activation of the polypeptide consisting of the amino acid sequence shown by SEQ ID NO:2 by each compound was 17.1 μmol/L, 22.5 μmol/L, and 7.0 μmol/L, respectively, in terms of $EC_{50}$.

From these results, it was found that allyl isothiocyanate, cinnamic aldehyde, and acrolein have the action of activating the polypeptide consisting of the amino acid sequence shown by SEQ ID NO:2 to allow calcium to flow into cells.

Example 5

Screening for TRPA1 Inhibitors

Compounds that inhibit a polypeptide consisting of the amino acid sequence shown by SEQ ID NO:2 (inhibitor) were screened for. Inhibitory activity was measured by performing detection of calcium inflow in the cells using a calcium-sensitive fluorescent reagent; specifically, the method described in Example 3 was used with a modification. As the screening criterion, compounds having an $IC_{50}$ of 100 μmol/L or less were selected. For inhibitor measurements, various compounds at 30 μM (final concentration at the time of reaction was 10 μM) were dispensed to a plate, and the plate was simultaneously set to FLIPR. After this pretreatment was performed, changes in intracellular calcium concentration after addition of cinnamic aldehyde were measured by with the FLIPR, and their inhibitory actions were investigated. Ruthenium Red was found to be a compound that inhibits the elevation of fluorescence intensity. The inhibitory activity of Ruthenium Red on the polypeptide consisting of the amino acid sequence shown by SEQ ID NO:2 was 2.2 μmol/L in terms of $IC_{50}$.

Example 6

Expression Analysis in Human Tissues

The expression of the TRPA1 gene in human tissue was analyzed by real time PCR using a sequence detector (PRISM7900; Applied Biosystems). By performing real time PCR, the desired gene contained in mRNA can be quantitatively measured.

From 1 μg of polyA$^+$RNA (CLONTECH Laboratories) derived from various human tissues, a reverse transcription reaction was carried out using random primers. A cDNA obtained by carrying out the reaction using the reverse transcriptase SuperScript II (GIBCO BRL) per the attached protocol was used in the experiment. With this first strand cDNA as the template, using a fluorescent reagent (SYBR Green PCR Core Reagents Kit; Applied Biosystems), PCR was performed. The aforementioned PCR was performed using an oligonucleotide consisting of the base sequence shown by SEQ ID NO:9 as a sense primer, and an oligonucleotide consisting of the base sequence shown by SEQ ID NO:10 as an antisense primer; first, thermal denaturation was performed at 95° C. (10 minutes), after which a cycle consisting of heat treatment at 95° C. (15 seconds)/59° C. (1 minute) was repeated 45 times. Each primer is a sequence specific for a gene consisting of the base sequence shown by SEQ ID NO:1.

Figure 2:
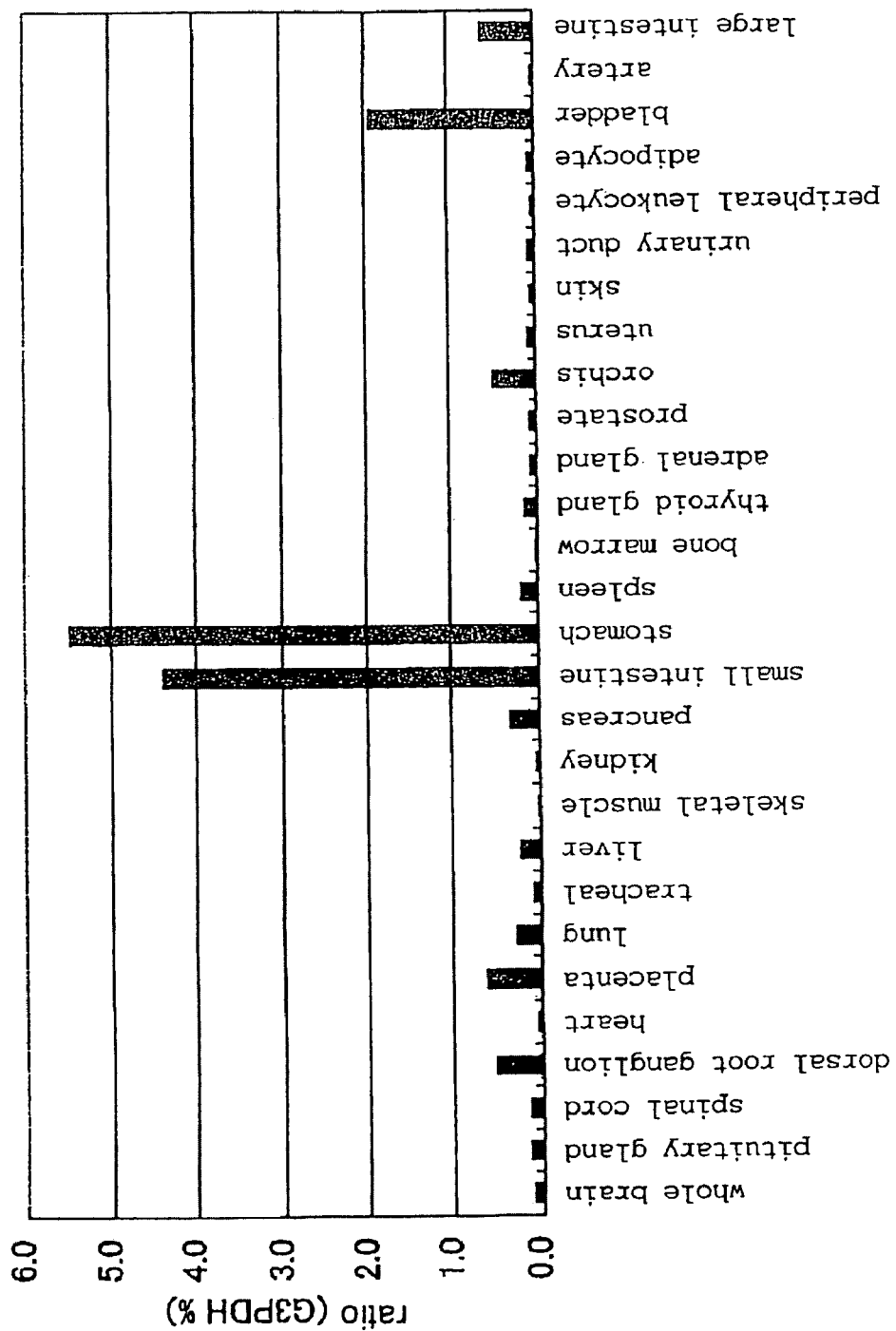
[FIG. 2] shows distributions of TRPA1 mRNA expression in various human tissues. The values shown are relative to the expression level of the human G3PDH gene as 100%.

The distributions of mRNA expression in various human tissues are shown in FIG. 2. High expression was detected in the stomach, small intestine, large intestine, urinary bladder and the like. From this finding, it was demonstrated that the mRNA consisting of the base sequence shown by SEQ ID NO:1 is expressed in digestive tissues such as the stomach, small intestine, and large intestine, and that the polypeptide consisting of the amino acid sequence shown by SEQ ID NO:2 functions in digestive tissues such as the stomach, small intestine, and large intestine.

Example 7

Expression Analysis in Mouse Tissues

RNA was prepared from mouse tissues as described below. A C57BL6 mouse (male, 8-week-old) was decapitated and exsanguinated, after which it was dissected with scissors, and the brain, stomach, small intestine, and large intestine were extirpated. These tissues were washed with ice-cooled physiological saline, after which they were homogenized by the addition of Isogen (Nippon Gene Co., Ltd.), and total RNA was prepared per the manual. For 1 μg of the extracted RNA, a first strand cDNA was synthesized using random primers per the manual of SuperScript II (Invitrogen), after which it was dissolved in 200 μl of TE.

Example 8

Expression Analysis in Mouse Tissues (Real Time PCR)

The expression of the TRPA1 gene in mouse tissues was analyzed by real time PCR using a sequence detector (PRISM7900; Applied Biosystems). With the mouse tissue first strand cDNA obtained in Example 7 above as the template, using a fluorescent reagent (SYBR Green PCR Core Reagents Kit; Applied Biosystems), PCR was performed. The aforementioned PCR was performed using an oligonucleotide consisting of the base sequence shown by SEQ ID NO:11 as a sense primer, and an oligonucleotide consisting of the base sequence shown by SEQ ID NO:12 as an antisense primer; first, thermal denaturation was performed at 95° C. (10 minutes), after which a cycle consisting of heat treatment at 95° C. (15 seconds)/59° C. (1 minute) was repeated 45 times. Each primer is a sequence specific for a gene consisting of the base sequence shown by SEQ ID NO:3. When these base sequences are translated, the amino acid sequence shown by SEQ ID NO:4 is obtained.

As a result, relative to the expression level of a reference standard of the mouse β actin gene as 100%, in the mouse stomach, jejunum, and large intestine, 0.037%, 0.084%, and 0.094%, respectively, of TRPA1 mRNA expressions were observed, whereas the expression level in the whole brain was 0.014%. From this finding, it was demonstrated that the TRPA1 mRNA consisting of the base sequence shown by SEQ ID NO:3 is expressed in the digestive tissues, and that a polypeptide consisting of the amino acid sequence shown by SEQ ID NO:4 is functioning.

Example 9

Expression Analysis in Rat Tissues (1) Rat Tissues
RNA was prepared from rat tissues as described below. A Wistar rat (male, 8-week-old) was decapitated and exsanguinated, after which it was dissected with scissors, and the brain, small intestine, and large intestine were extirpated. These tissues were washed with ice-cooled physiological saline, and the small intestine and large intestine were separated into the mucosal layer and the smooth muscle layer using glass slides. These tissue samples were homogenized by the addition of Isogen (Nippon Gene Co., Ltd.), and total RNA was prepared per the manual. For 1 μg of the extracted RNA, a first strand cDNA was synthesized using random primers per the manual of SuperScript II (Invitrogen), after which it was dissolved in 200 μl of TE.
(2) Cultured Cells and Medium
RIN14B cells (rat pancrease-derived endocrine cell line) were purchased from ATCC. The RIN14B cells were cultured using an RPMI1640 medium (Invitrogen) containing 10% fetal bovine serum (Invitrogen) unless otherwise stated. The RIN14B cells were cultured using an RPMI1640 medium (Invitrogen) containing 10% FCS until they became pre-confluent, and they were used for experiments such as gene expression analysis.
(3) Isolation of Rat Small Intestine EC Cells
A Wistar rat (male, 8-week-old) was decapitated and exsanguinated, after which it was dissected and laparotomized with scissors, and the small intestine was extirpated. The inside of the lumen of the extirpated small intestine was washed with physiological saline, and about 20 mL of Buffer A (70 mM NaCl, 5 mM KCl, 20 mM NaHCO$_3$, 0.5 mM NaH2PO4, 50 mM HEPES (pH 7.2), 11 mM glucose, 3 mM EDTA, 0.5% BSA, 0.05 mM dithiothreitol, 1 mg/mL N-acetyl-L-cysteine) was injected, after which both ends were closed, and the small intestine was allowed to stand in 37° C. incubated HBSS for 10 minutes. Thereafter, the Buffer A in the lumen of the small intestine was discarded, about 20 mL of Buffer A was injected again, and the small intestine was allowed to stand in 37° C. incubated HBSS for 10 minutes. Again, the Buffer A in the lumen of the small intestine was discarded, fresh Buffer A was injected, and the small intestine was allowed to stand in 37° C. incubated HBSS for 20 minutes, after which the lumen content was recovered. This operation was repeated three times in total, all the lumen contents were combined together, and this was used as the small intestine mucosal epithelial cell sample.

Next, an EC cell fraction was prepared using counterflow centrifugal elutriation (CCE). A CCE apparatus (BECKMAN, JE-5.0) was operated at a fixed rotor speed of 2000 rpm, with a PBS containing 1% fetal bovine serum, 1% glucose, 1 mM dithiothreitol, and 1 mM EDTA used as the buffer for CCE. A small intestine mucosal epithelial cell sample was injected to the CCE apparatus, and the cells flowing out at 21 mL/min were recovered, after which the sample was further purified by density gradient centrifugation using a Percoll solution (d=1.132 g/mL, Pharmacia). A 9-fold volume of the Percoll solution was added to a 10-fold concentration of HBSS, and this was used as the 100% Percoll solution. The 100% Percoll was diluted with a 1-fold concentration of HBSS to yield a 60% Percoll solution, a 30% Percoll solution, and a 20% Percoll solution, which were overlain in a centrifugal tube. Furthermore, the CCE-purified sample was overlain thereon, and centrifuged at 1100 rpm for 10 minutes. The cells gathering in the interface between the 60% Percoll solution and the 30% Percoll solution were recovered and washed with PBS, and this was used as the EC cell fraction. This EC cell fraction was assayed to determine the expression levels of the marker genes for TPH1, chromogranin A, synaptophysin, and VMAT1 by real time PCR method; samples confirmed to exhibit marker gene expression levels not less than 20 times higher than the level for a small intestine mucosal epithelial cell sample were used in the experiments that followed (Table 1).

The aforementioned operation was performed per the protocol attached to the elutriator system, and a commonly known method (Shunsuke Migita edt., "Men-eki Jikken Sousahou 2", 1995, Nankodo).
(4) Extraction of RNA and Synthesis of cDNA
For the RIN14B cells and the rat EC cell fraction, the cells were isolated and counted, after which total RNA was extracted and purified per the manual of the RNeasy mini KIT (QIAGEN). For 1 μg of the extracted RNA, a first strand cDNA was synthesized using random primers per the manual of SuperScript II (Invitrogen), after which it was dissolved in 200 μl of TE.

Example 10

Expression Analysis in Rat Tissues (Real Time PCR)

The expression of the TRPA1 gene in rat tissues, a rat EC cell fraction and RIN14B cells was analyzed by real time PCR using a sequence detector (PRISM7900; Applied Biosystems). With the first strand cDNA derived from rat tissue, rat EC cells or RIN14B cells, obtained in the aforementioned Example, as the template, using a fluorescent reagent (SYBR Green PCR Core Reagents Kit; Applied Biosystems), PCR was performed. The aforementioned PCR was performed using an oligonucleotide consisting of the base sequence shown by SEQ ID NO:13 as a sense primer, and an oligonucleotide consisting of the base sequence shown by SEQ ID NO:14 as an antisense primer; first, thermal denaturation was performed at 95° C. (10 minutes), after which a cycle consisting of heat treatment at 95° C. (15 seconds)/59° C. (1 minute) was repeated 45 times. Each primer is a sequence specific for a gene consisting of the base sequence shown by SEQ ID NO:5. When these sequences are translated into amino acid sequences, the amino acid sequence shown by SEQ ID NO:6 is obtained.

As a result, relative to the expression level of a reference standard of the rat G3PDH gene as 100%, in the rat large intestine mucosa and small intestine mucosa, 0.79% and 0.85%, respectively, of TRPA1 mRNA expressions were observed, whereas the expression level in the brain was 0.11%. From this finding, it was demonstrated that TRPA1 is highly expressed in the rat gut and functions. In small intestine EC cells, a high expression level of TRPA1 mRNA was detected as with other EC cell markers, demonstrating that TRPA1 is expressed in the EC cells (Table 1). Furthermore, the RIN14B cells showed expression of the EC cell marker gene, and the TRPA1 gene, to equivalent or higher extent than the EC cells, demonstrating that RIN14B cells have properties very similar to those of EC cells (Table 2).

TABLE 1

Expression levels of TRPA1 mRNA and EC cell marker genes in rat small intestine EC cell fraction
Ratio (% of small intestine mucosal tissue)

|  | Small intestine mucosal tissue | EC cell fraction |
|---|---|---|
| TPH1 | 100 | 7310.5 |
| Chromogranin A | 100 | 7837.2 |
| VMAT 1 | 100 | 3777.6 |
| Synaptophysin | 100 | 2288.4 |
| TRPA1 | 100 | 1626.7 |

The values are relative to the expression level of each gene in rat small intestine mucosal tissue as 100%.

TABLE 2

Expression levels of TRPA1 mRNA and EC cell marker genes in digestive endocrine cell-derived RIN14B cell line

| (ratio) | TPH1 | chromograinA | VMAT1 | synaptophysin | TRPA1 |
|---|---|---|---|---|---|
| Small cell EC cell fraction | 100.0 | 100.0 | 100.0 | 100.0 | 100.0 |
| RIN14B | 917.4 | 72646.8 | 3442.6 | 98.8 | 159.7 |

The values are relative to the expression level of each gene in rat EC cell fraction as 100%.

Example 11

Expression Analysis in Human Tissue (In Situ Hybridization/Immunohistochemical Staining)

To confirm the expression of TRPA1 in human EC cells, in situ hybridization staining was performed using the human duodenum.

Paraffin-embedded human duodenum tissue (CYTOMYX) was sectioned to 6 μm thickness, and this was used as the sample for in situ hybridization staining.

With the plasmid pcDNA-human TRPA1 obtained in Example 1 as the template, by the in vitro transcription method, a digoxigenin-labeled RNA antisense probe was prepared. Digoxigenin labeling was performed using a commercially available reagent (DIG RNA Labeling Mix; Roche) per the attached protocol. For negative control, using the same method, a digoxigenin-labeled RNA sense probe was also prepared. The probe sequence used was the same region as the 2870th to 3360th base sequence of the human TRPA1 gene sequence shown by SEQ ID NO:1.

Using the sample and probe obtained above, in situ hybridization staining was performed. The antibody used was an alkaline phosphatase-labeled anti-digoxigenin antibody (Roche), and the color development substrate used was NBT/BCI (mixed liquid of 5-bromo-4-chloro-3-indoylphosphoric acid and nitro blue tetrazolium salt); after color development, nuclear staining was performed with kernechtrot.

Figure 3:
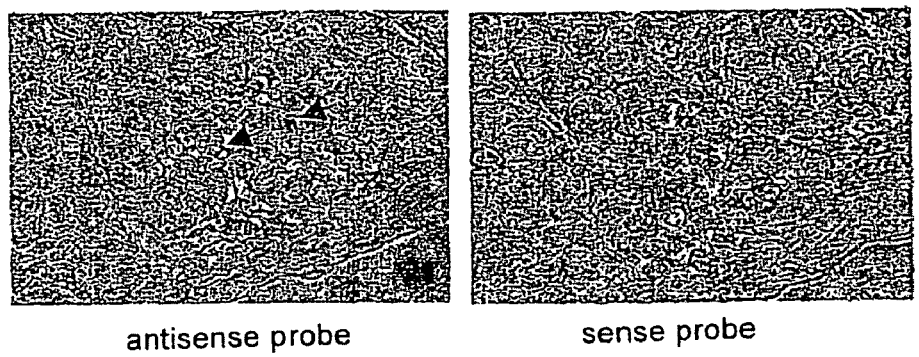
[FIG. 3] shows the results of in situ hybridization staining of the TRPA1 gene using the human duodenum. In an investigation using an antisense probe, intense color development was found in some cells in the epithelium of the human duodenum (left panel; arrow). On the other hand, in an investigation using a sense probe, no staining was observed (right panel).

As a result, in the investigation using the antisense probe, intense color development was observed specifically in some cells in the epithelium of the human duodenum. In the investigation using the sense probe, no staining was observed. From these results, it was demonstrated that the human TRPA1 gene, which consists of the base sequence shown by SEQ ID NO:1, is expressed in the cells in the gut lacuna also in humans (FIG. 3).

Example 12

Expression Analysis in Human Tissue (In Situ Hybridization/Immunohistochemical Staining)

To determine whether or not the TRPA1 expression site observed in Example 11 was EC cells, in situ hybridization is staining was performed using the human duodenum, after which immune staining was performed with an anti-serotonin antibody.

Figure 4:
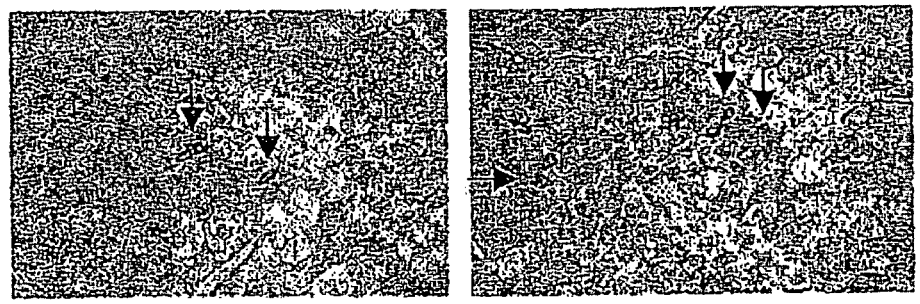
[FIG. 4] shows the results obtained by performing in situ hybridization staining of the TRPA1 gene using the human duodenum, and then immunologically staining the same section with an anti-serotonin antibody. Cells that concurrently expressed TRPA1 and serotonin are shown by the arrow.

After TRPA1 was stained by in situ hybridization of the human duodenum by the same method as Example 11, a reaction was carried out using an anti-serotonin antibody (Sigma) as the primary antibody. Furthermore, a reaction was carried out using a biotinized anti-rabbit IgG antibody as the secondary antibody, after which a color developing reaction was carried out using DAB as the color development substrate. As a result, the epithelial cells of the human duodenum, which showed the expression of TRPA1, also showed color development by the serotonin antibody. From these results, it was demonstrated that the TRPA1 gene, consisting of the base sequence shown by SEQ ID NO:1, is expressed in the serotonin-expressing epithelial cells of the human duodenum, that is, EC cells (FIG. 4).

Example 13

Detection of Channel Activity in RIN14B Cells Using Calcium-sensitive Fluorescent Reagent RIN14B cells ($5\times10^4$ cells), wherein the expression of TRPA1 was confirmed in Example 10, were incubated in the presence of a calcium-sensitive fluorescent reagent (Fluo3-AM; DOJINDO) at 37° C. for 1 hour to thereby incorporate the calcium-sensitive fluorescent reagent in the cells, after which the cells were washed with physiological saline to remove the calcium-sensitive fluorescent reagent that had not been incorporated in the cells. To the cells obtained, physiological saline supplemented with allyl isothiocyanate, cinnamic aldehyde, or acrolein was added; the fluorescence emitted by the cells was measured over time. The above-described measurements were performed using an automated fluorescence detection apparatus (FLIPR; Molecular Device). Using physiological saline not supplemented with allyl isothiocyanate, cinnamic aldehyde, or acrolein, the same operation was performed. Ruthenium Red was added concurrently and a measurement was performed to determine whether or not calcium inflow in the cells was be inhibited.

As a result, in RIN14B cells having allyl isothiocyanate, cinnamic aldehyde, or acrolein added thereto, an elevation of fluorescence intensity was detected from soon after the addition. On the other hand, in the investigation using physiological saline not supplemented with allyl isothiocyanate, cinnamic aldehyde, or acrolein, no fluorescence was detected in any case. This shows that TRPA1 was activated by allyl isothiocyanate, cinnamic aldehyde, and acrolein to allow calcium to flow into the cells. Furthermore, changes in intracellular $Ca^{2+}$ concentration with the addition of various concentrations of allyl isothiocyanate, cinnamic aldehyde, and acrolein to RIN14B cells were examined; it was demonstrated that they concentration-dependently allow calcium to flow into the cells.

When Ruthenium Red was added, the elevation of fluorescence intensity was inhibited by allyl isothiocyanate, cinnamic aldehyde, and acrolein (30 µM Ruthenium Red 90.9% inhibited the activation by allyl isothiocyanate).

Example 14

Measurements of Serotonin Secretion from RIN14B

To determine whether or not TRPA1 is involved in serotonin release, the promotion of serotonin secretion from RIN14B by TRPA1 activators was measured.

After RIN14B cells in culture in a Petri dish were detached using a PBS containing 1 mM EDTA, they were sown to a 96-well plate and cultured for 2 days. The medium used was RPMI1640 (Invitrogen Japan K.K.) supplemented with 10% fetal bovine serum (ICN), 100 U/ml penicillin, and 100 µg/ml streptomycin. After the cells were once washed with Hanks' Balanced Salt Solutions (HBSS, Invitrogen) supplemented with 0.1% BSA and 10 µM fluoxetine (TOCRIS), each TRPA1 activator, previously diluted/prepared with the above-described HBSS, was added, and the RIN14B cells were cultured at 37° C. in the presence of 5% $CO_2$ for 20 minutes. After the cultivation, the cell supernatant was recovered, and stored under freezing. The serotonin content in the supernatant was measured using a commercially available serotonin immunoassay kit (Beckman).

Figure 5:
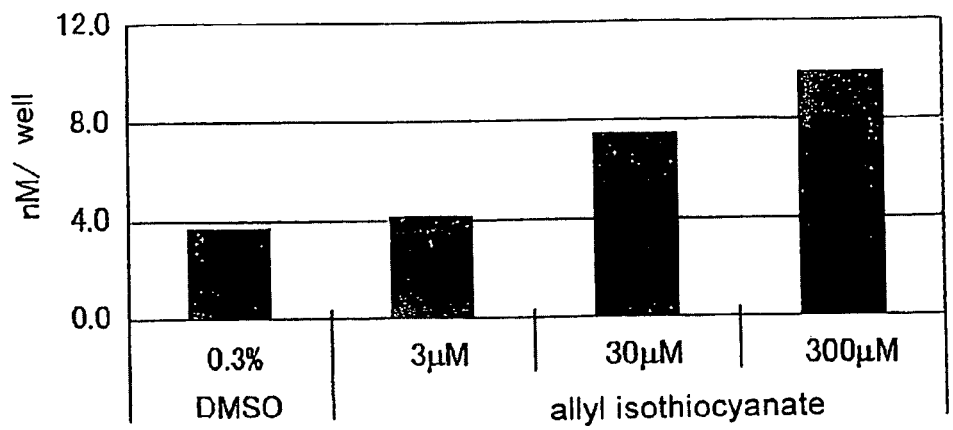
[FIG. 5] shows the results of measurements of the amount of serotonin released when each of allyl isothiocyanate, cinnamic aldehyde, and acrolein was added to RIN14B cells. Each of them concentration-dependently promoted the release of serotonin from the RIN14B cells.
Figure 5:
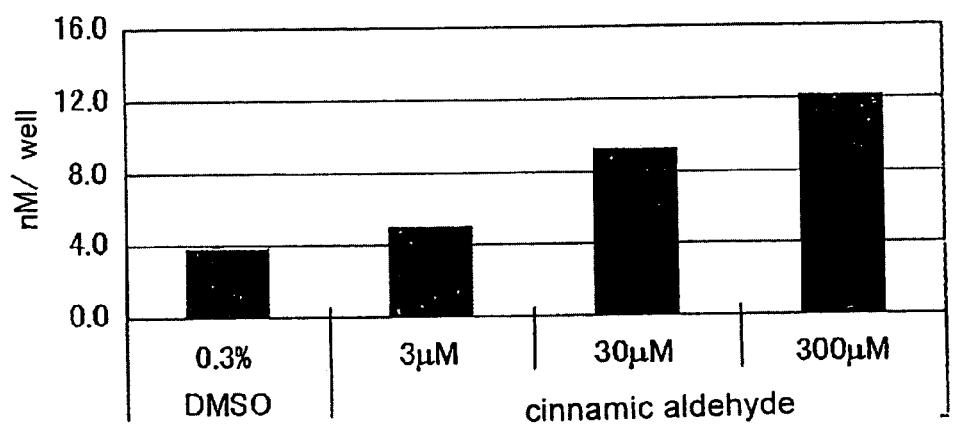
Figure 5:
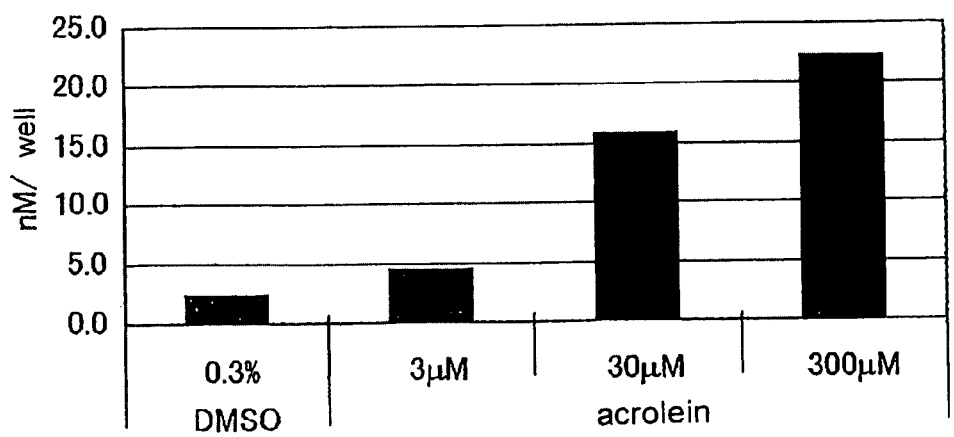

As a result, as shown in FIG. 5, serotonin secretion was promoted by allyl isothiocyanate, cinnamic aldehyde, and acrolein, all of which exhibited remarkable activities in an intracellular calcium ion inflow assay using RIN14B cells. On the other hand, when the cells were treated with Ruthenium Red concurrently with acrolein (30 µM), Ruthenium Red concentration-dependently suppressed acrolein-induced serotonin secretion (73.0% inhibited by 30 µM Ruthenium Red); when the cells were treated with Ruthenium Red (30 µM) concurrently with cinnamic aldehyde (30 µM), Ruthenium Red completely suppressed cinnamic aldehyde-induced serotonin secretion. From these results, it was demonstrated that TRPA1 is involved in the action of promoting serotonin secretion from RIN14B cells.

Example 15

Suppression of Expression of the Rat TRPA1 Gene by Introduction of an siRNA Specific for Rat TRPA1 Sequence RIN14B cells were sown to a 60 mm Petri dish at $6\times10^5$ cells and cultured for 1 day. After various sequences of siRNA for rat TRPA1 (10 nM), designed using the siRNA design system siDirect (RNAi), were introduced using a transformation reagent (LIPOFECTAMINE2000; Invitrogen Japan K.K.), the RIN14B cells were further cultured for 2 days, and the expression level of the rat TRPA1 gene was measured. Detection of the expression level of the rat TRPA1 gene was attempted by the method of Example 10. As a result, by adding #971, a rat TRPA1-specific siRNA (sense strand was SEQ ID NO:15, antisense strand was SEQ ID NO:16), to the RIN14B cells, a reduction in the expression level of the rat TRPA1 was observed. From this finding, it was found that #971 specifically suppressed the expression of the rat TRPA1 gene.

Example 16

Suppressive Effect on the Intracellular Calcium Inflow Activity of Allyl isothiocyanate in siRNA-introduced RIN14B In Example 15, it was confirmed that #971, a TRPA1-specific siRNA, remarkably suppressed the expression of rat TRPA1. An investigation was performed on intracellular calcium inflow activity in RIN14B cells having #971 introduced thereto by the method of Example 15. As a result of an examination of the intracellular calcium inflow activity of allyl isothiocyanate by the method of Example 13, in RIN14B having #971 introduced thereto, the intracellular calcium inflow activity of allyl isothiocyanate (300 µM) was suppressed by 67.3%. On the other hand, it was shown that in RIN14B having the negative control siRNA, a random sequence siRNA, introduced thereto, the intracellular calcium inflow activity of the above-described activator was retained. From this result as well, it was confirmed that TRPA1 is also involved in the intracellular calcium inflow activity of allyl isothiocyanate.

Example 17

Figure 6:
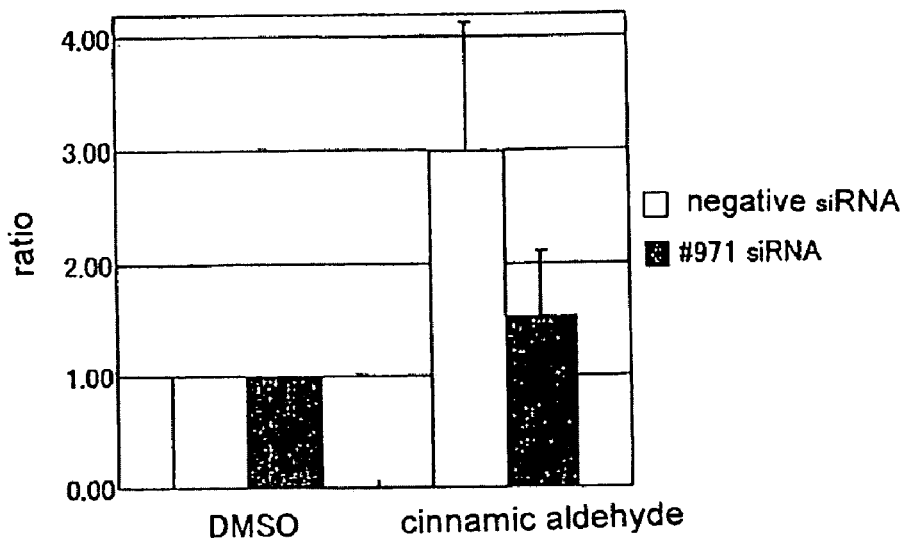
[FIG. 6] shows the results of measurements of the amount of serotonin released when an siRNA of TRPA1 was introduced to RIN14B cells. #971 siRNA of TRPA1 suppressed cinnamic aldehyde-induced serotonin release from the RIN14B cells (mean±SD).

Suppressive Effect on the Serotonin Secretion Promoting Activity of Cinnamic Aldehyde in siRNA-introduced RIN14B In Example 16, it was confirmed that #971, a TRPA1-specific siRNA, remarkably suppressed the expression of rat TRPA1, and also suppressed intracellular calcium inflow. Hence, in RIN14B cells having #971 introduced thereto by the method of Example 15, serotonin secretion increasing activity was investigated. As a result of an examination of the serotonin secretion increasing activity of cinnamic aldehyde by the method of Example 14, as shown in FIG. 6, in RIN14B having #971 introduced thereto, the serotonin secretion increasing activity of cinnamic aldehyde was suppressed. On the other hand, in RIN14B having the negative control siRNA, a random sequence siRNA, introduced thereto, it was shown that the serotonin secretion promoting activity of the above-described activator was retained. From this result, it was proven that TRPA1 is involved in the promotion of serotonin secretion.

Example 18

Measurements of Serotonin Secretion from Rat EC Cells

Serotonin secretion activity in EC cells prepared by the method described in Example 9-(3) was measured by a method modified from the method of Example 14 above. A prepared rat EC cell fraction was once washed with a Hanks' Balanced Salt Solution (HBSS, Invitrogen) supplemented with 0.1% BSA, after which a TRPA1 activator, previously diluted/prepared with the above-described HBSS, was added, and the cells were cultured at 37° C. in the presence of 5% $CO_2$ for 45 minutes. After the cultivation, the cell supernatant was recovered and stored under freezing.

Figure 7:
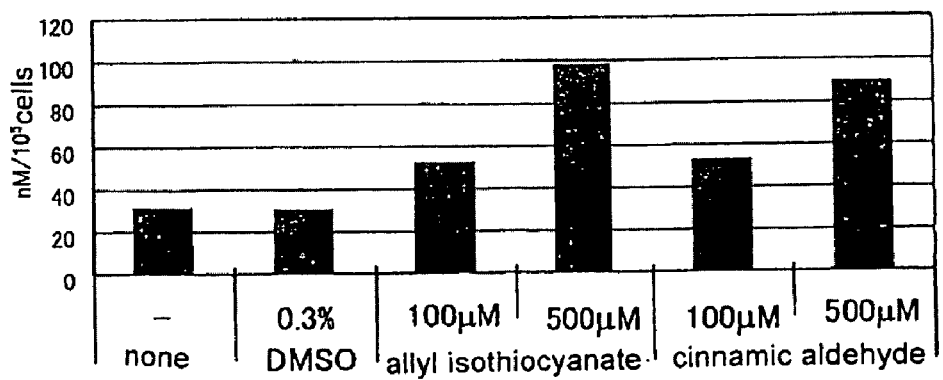
[FIG. 7] shows the results of measurements of the amount of serotonin released when EC cells purified from the rat small intestine were treated with allyl isothiocyanate and cinnamic aldehyde. Both allyl isothiocyanate and cinnamic aldehyde promoted the release of serotonin from the EC cells.

The serotonin content in the supernatant was measured using a commercially available serotonin immunoassay kit (Beckman). As a result, as shown in FIG. 7, in rat EC cells, like in RIN14B, significant serotonin secretion promoting activity was observed with allyl isothiocyanate and cinnamic aldehyde. From the results above, it was proven that TRPA1 is responsible for the action of promoting serotonin secretion not only from RIN14B cells, but also from EC cells.

Example 19

Measurements of Isolated Guinea Pig Gut Constriction Activity

Guinea pigs (Hartley strain, male, weighing 300-400 g), under ether anesthesia, were exsanguinated to death by cutting the carotid artery. The ileum was extirpated, about 15-cm portions at both ends were removed, a section 1.5 cm long was cut out from the remaining portion, and incisions were made longitudinally parallelly in the gut to prepare a tabular specimen. This specimen was sandwiched with serrefine at both ends, and suspended with a thread in a Magnus chamber containing 10 ml of a 37° C. Krebs solution (118 mM NaCl, 4.7 mM KCl, 2.5 mM $CaCl_2$, 1.2 mM $MgSO_4$, 1.2 mM $KH_2PO_4$, 11 mM D-glucose, 20 mM $NaHCO_3$) aerated with 95% $O_2$-5% $CO_2$ mixed gas. A 1-g load was applied to the specimen, buffers were exchanged at 15-minute intervals, and the specimen was allowed to stand for about 60 minutes to stabilize its tension. Changes in the tension in response to agonist stimulation were measured isometrically, and recorded on a recorder. Acetylcholine, $10^{-5}$ M, was administered to induce contraction of the ileum specimen; after the contraction maximized, the bath was washed three times to purge out the acetylcholine. This operation was repeated at 10-minute intervals, and after the induced contraction stabilized two consecutive times, each test substance was administered. By comparing the contractile forces produced by acetylcholine and the test substance, the effect of the test substance was evaluated. One specimen was investigated only at one concentration of the test substance. (1) For each of allyl isothiocyanate, cinnamic aldehyde, and acrolein, an investigation was made by single-dose administration at four concentrations: 10 μM, 30 μM, 100 μM, and 300 μM. As a result, constrictive action was observed at 100 μM or more for allyl isothiocyanate and cinnamic aldehyde, and at 10 μM or more for acrolein (Table 3). From the results above, it was shown that the TRPA1 activator induced gut contraction.

TABLE 3

Dose-dependent constrictive actions of allyl isothiocyanate, cinnamic aldehyde, and acrolein

| | Magnus (guinea pig ileum) | |
| --- | --- | --- |
| | Action | $EC_{50}$(μM) † |
| Allyl isothiocyanate | Contraction | 129.0 |
| Cinnamic aldehyde | Contraction | 88.3 |
| Acrolein | Contraction | 70.3 |

(† Calculated relative to constrictive reaction at 300 μM as 100%)

(2) Antagonization Experiments with TRPA1 Inhibitor (Ruthenium Red)

The inhibitory action of the TRPA1 receptor inhibitor Ruthenium Red (30 μM) on contraction upon stimulation with allyl isothiocyanate (300 μM) was investigated. For each of two different specimens from the same individual, either a vehicle or Ruthenium Red (30 μM) was applied for 15 minutes, after which contraction upon stimulation with allyl isothiocyanate (300 μM) was measured. As a result, in the Ruthenium Red-applied specimen, the contraction upon stimulation with allyl isothiocyanate was suppressed by about 84% compared to the vehicle-applied specimen. From the results above, it is suggested that allyl isothiocyanate may induce gut contraction via the TRPA1 receptor.

(3) Inhibition Experiments with Serotonin Receptor Antagonists

The inhibitory actions of various serotonin receptor antagonists on contraction upon stimulation with allyl isothiocyanate (300 μM) were investigated. The serotonin receptor antagonists used were pizotifen maleate (10 μM), a 5-HT1,2 receptor antagonist, ketanserin tartrate (0.1 μM), a 5-HT2 receptor antagonist, ramosetron hydrochloride (0.3 μM), a 5-HT3 receptor antagonist, and GR113808 (0.3 μM), a 5-HT4 receptor antagonist. In different specimens from the same individual, a vehicle or each serotonin antagonist was applied for 15 minutes, after which contraction upon stimulation with allyl isothiocyanate (300 μM) was measured. As a result, in the pizotifen maleate-applied specimen and ramosetron hydrochloride-applied specimen, contraction upon stimulation with allyl isothiocyanate was suppressed by about 44% and about 74%, respectively, compared to the vehicle-applied specimen. From the results above, it was shown that serotonin was released upon stimulation with allyl isothiocyanate to induce contraction via serotonin receptors such as 5-HT1 receptor and 5-HT3 receptor.

The inhibitory actions of various serotonin receptor antagonists on contraction upon stimulation with acrolein (300 μM) were investigated in the same manner. As a result, in the pizotifen maleate-applied specimen and ramosetron hydrochloride-applied specimen, contraction upon stimulation with allyl isothiocyanate was suppressed by about 74% and about 84%, respectively, compared to the vehicle-applied specimen. From the results above, it was shown that serotonin was released upon stimulation with acrolein to induce contraction via serotonin receptors such as 5-HT1 receptor and 5-HT3 receptor.

From the results obtained in the Examples above, it was demonstrated that TRPA1 is highly expressed in the digestive tract, particularly in the gut EC cells. Furthermore, as a result of an extensive investigation using a TRPA1 activator and inhibitor obtained by performing compound screening, it was demonstrated that TRPA1 activation causes serotonin release from gut EC cells, and causes gut contraction via the released serotonin. Next, in the Examples below, a test was performed to determine whether the TRPA1 activator has the action of accentuating digestive tract movement in vivo.

Example 20

Measurements of the Action of Accentuating Dog Digestive Tract Movement

Figures 1, 8:
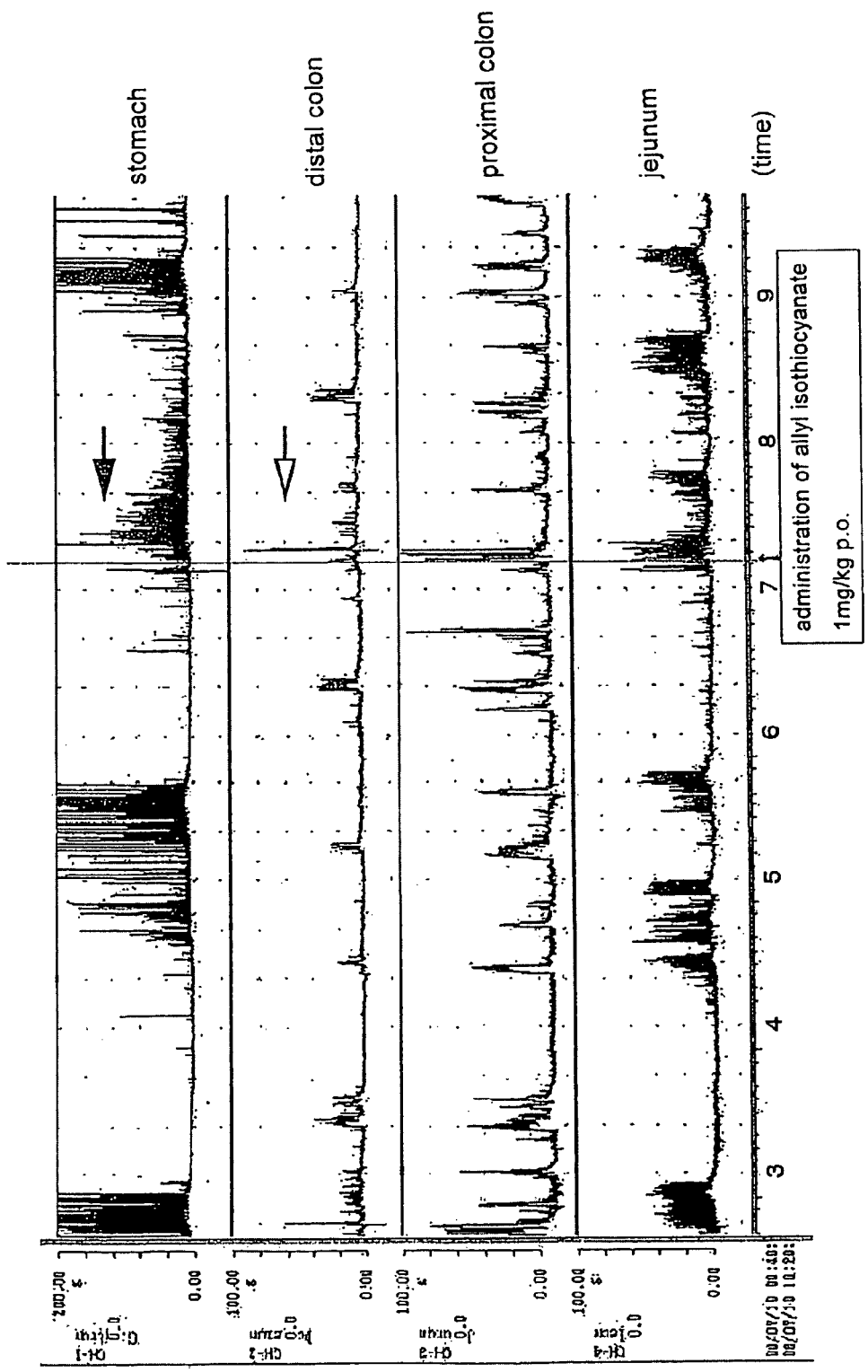
Figures 2, 8:
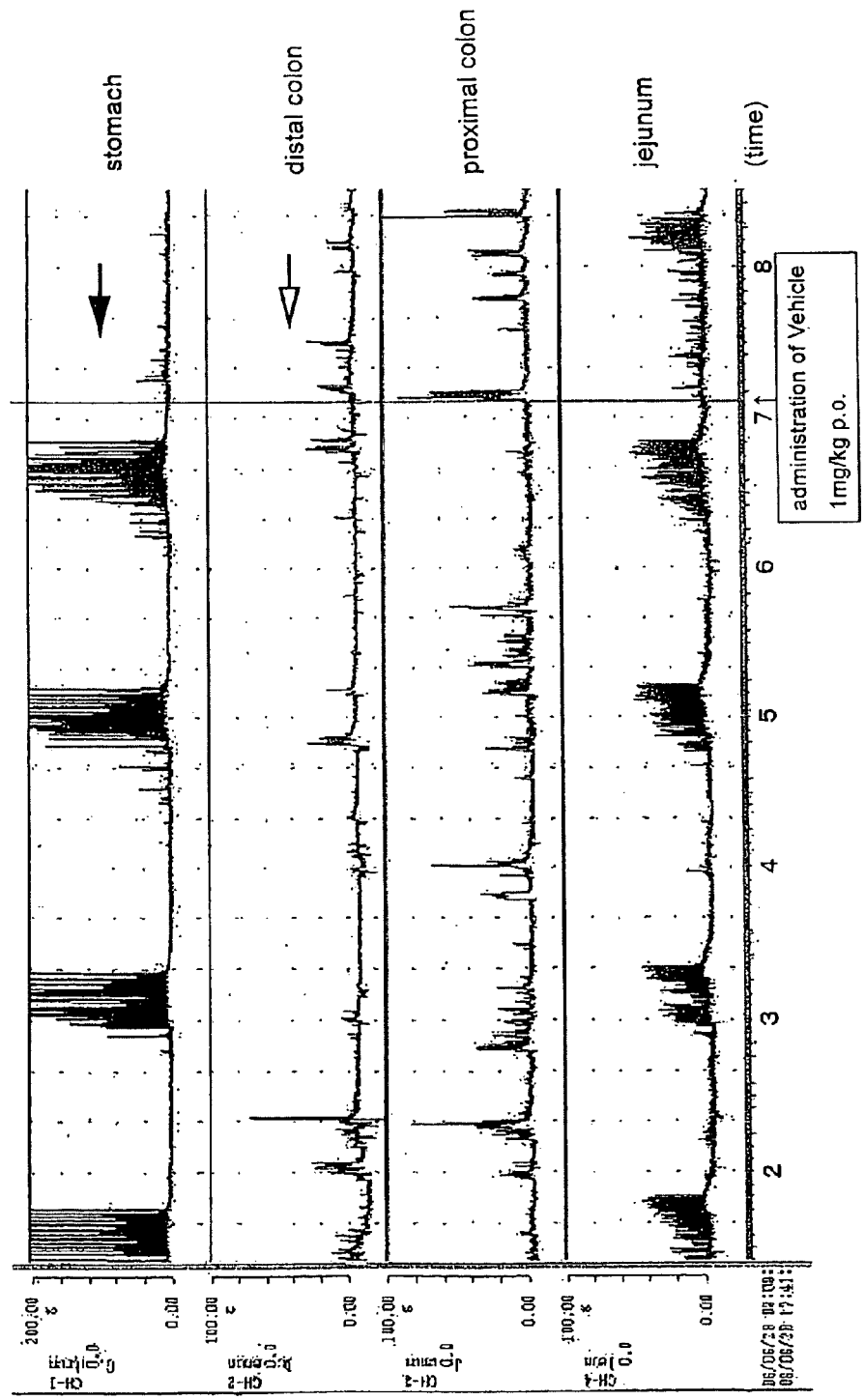

Measurements of digestive tract movement were performed by the strain gauge force transducer method. Dogs (beagle dogs, male, 11-13 kg), fasted for 24 hours, under pentobarbital sodium anesthesia, had a strain gauge force transducer (F-12IS, Star Medical, Inc., Tokyo) sutured to a total of four sites, i.e., a portion 5 cm from the pylorus toward the mouth (gastric vestibule), a portion 20 cm from the Treiz ligament toward the anus (jejunum), a portion 10 cm from the ileocecal opening toward the anus (proximal colon), and a portion 10 cm from the anus toward the mouth (distal colon), in a way that allowed examination of contraction along the orbicular muscle. After recovery for 1 week or more postoperatively, experiments were preformed. Measurements of digestive tract movement were performed using a telemeter system (DAT-80RA, Star Medical, Inc.). Allyl isothiocyanate was administered orally about 20 minutes after phase-III-like digestive tract movement in the stomach was measured after regular expression of IMC (Inter digestive migrating motor complex) was confirmed by a measurement of digestive tract movement in animals previously fasted for 17 hours or more. As a result, as shown in FIG. 8-1, allyl isothiocyanate (1, 10 mg/kg) induced colon GMC (Giant migrating contraction) within 10 minutes after administration; it is suggested that allyl isothiocyanate, a TRPA1 activator, might accentuate digestive tract movement to induce defecation. On the other hand, as shown in FIG. 8-2, in the vehicle group, induction of GMC was not observed.

Because 5-HT is known to accentuate water secretion from the digestive tract, if a TRPA1 activator secretes 5-HT via gut EC cells, it is expected to accentuate water secretion from the digestive tract. Hence, an actual test was performed to determine whether or not a TRPA1 activator has the action of accentuating water secretion from the digestive tract.

Example 21

Measurement of Mouse Gut Water Secretion Secretion Accentuating Action

Figure 9:
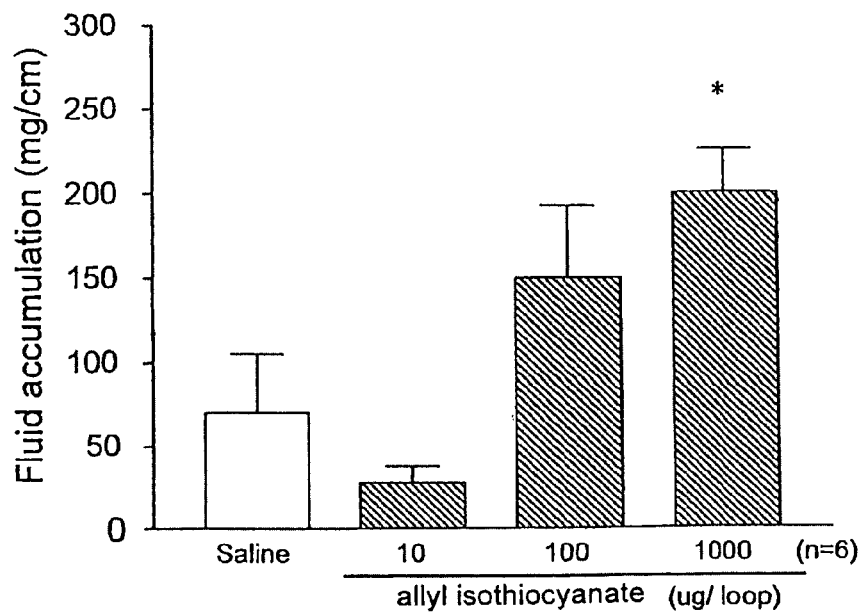
[FIG. 9] shows the results of a measurement of the action of allyl isothiocyanate in an experiment to measure digestive tract water secretion. Allyl isothiocyanate concentration-dependently accentuated water secretion compared to the vehicle control. (N=6, mean±SE)
*: $p<0.01$ vs saline group (Dunnett's test)

Mice (ddy, male, 35-42 g, SLC), fasted overnight, were anesthetized with pentobarbital (50 mg/kg i.p.) and laparotomized, and ileum tissue about 2 cm in the vicinity of the cecum was ligated with a thread at both ends to prepare an ileum loop. 100 µL of saline or allyl isothiocyanate, a TRPA1 activator (10, 100, 1,000 µg), was administered into the loop. After the administration, the gut was returned to the original position, and the abdominal muscle and the skin were sutured. Six hours after the treatment, each mouse was killed by cervical dislocation, after which the ileum loop was extirpated, and the content was weighed. As a result, allyl isothiocyanate dose-dependently accentuated water secretion from the gut, with significant water secretion accentuating action observed in the 1,000 µg dose group (FIG. 9).

Example 22

Evaluation of Allyl Isothiocyanate Using a Mouse Constipation Model

Because loperamide, a µ opioid receptor agonist, induces convulsive contraction in the gut and causes a delay of gut transportation, this experimental system is thought to be an experimental model of constipation type irritable bowel syndrome. Hence, an investigation was performed to determine whether or not allyl isothiocyanate, a TRPA1 activator, is effective in this constipation model.

Figure 10:
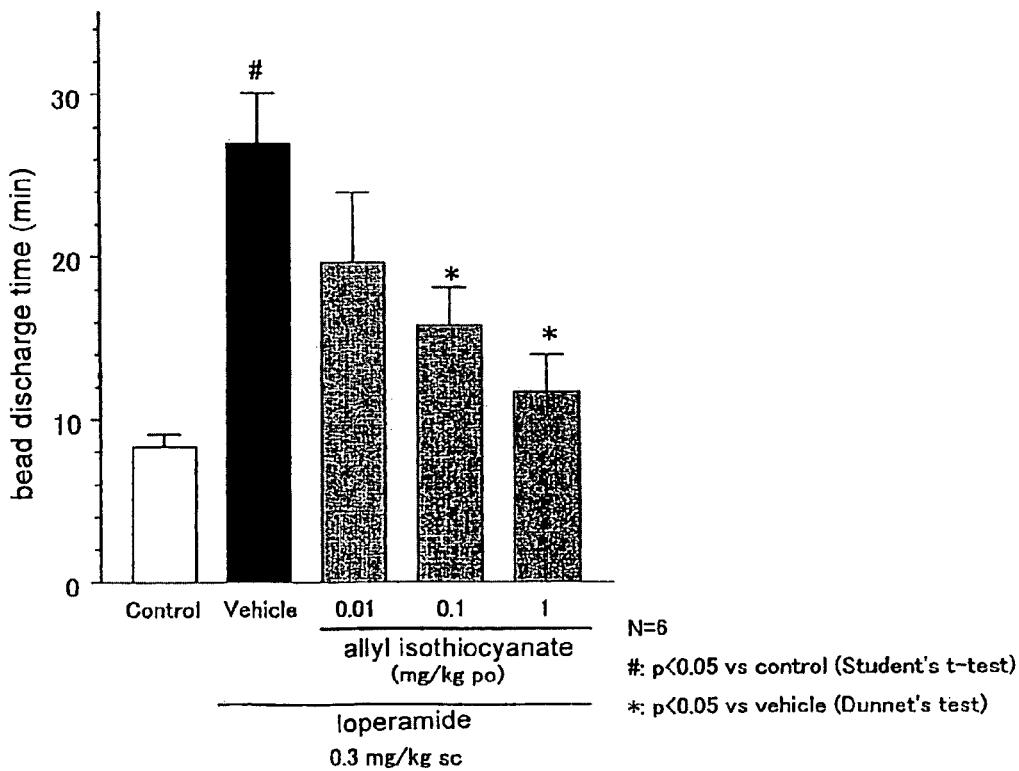
[FIG. 10] shows the results of a measurement of the action of allyl isothiocyanate in a loperamide-induced constipation model. Allyl isothiocyanate concentration-dependently shortened bead discharge time compared to the vehicle control. (N=6, mean±SE)
: $p<0.05$ vs control (Student's t-test), *: $P<0.05$ vs vehicle (Dunnett's test)

Mice (ddY, male, 5-week-old, SLC) were fasted from afternoon of the day before the experiment; on the day of the experiment, the mice were acclimated to the measurement cage for 1 hour or more, after which loperamide, 0.3 mg/kg, was administered subcutaneously. After 30 minutes, allyl isothiocyanate, a TRPA1 agonist, 0.01 to 1 mg/kg, was administered orally, just after which each mouse was anesthetized with ether, and had glass beads 3 mm in diameter inserted to a position 2 cm from the anus. The mouse was returned to the measurement cage, and time from awakening to discharge of the glass beads was measured. As a result, as shown in FIG. 10, a delay in bead discharge time was observed in the loperamide-dosed group (vehicle group), compared to the loperamide-non-dosed group (control group). Allyl isothiocyanate, a TRPA1 agonist, dose-dependently ameliorated the delay of bead discharge time by loperamide. From the results above, it is suggested that the TRPA1 activator might be effective against constipation type irritable bowel syndrome.

While the present invention has been described along with specific embodiments, modifications and improvements obvious to those of ordinary skill in the art are encompassed in the scope of the present invention.

This application is based on patent application No. 2006-275837 filed in Japan (filing date: Oct. 6, 2006), and the contents disclosed therein are hereby entirely incorporated by reference. In addition, the contents disclosed in any publication cited herein, including patents and patent applications, are hereby incorporated in their entireties by reference, to the extent that they have been disclosed herein.

The invention claimed is:

1. A screening method for a prophylactic and/or therapeutic drug for digestive organ diseases, comprising evaluating a test substance to determine whether or not the test substance is capable of regulating the channel activity of transient receptor potential cation channel, subfamily A, member 1 ("TRPA1") and determining whether or not the test substance is effective as a prophylatic and/or therapeutic drug for a digestive organ disease, wherein the TRPA1 comprises the amino acid sequence of SEQ ID NO: 2, SEQ ID NO: 4 or SEQ ID NO: 6, or an amino acid sequence that has 95% or more sequence identity to the amino acid sequence of SEQ ID NO: 2.

2. The screening method of claim 1, wherein the screening method is performed using a TRPA1 activator or a TRPA1 inhibitor.

3. The screening method of claim 1, wherein the regulation of the channel activity of TRPA1 is promotion of the channel activity of TRPA1.

4. The screening method of claim 1, wherein the regulation of the channel activity of TRPA1 is suppression of the channel activity of TRPA1.

5. The screening method of claim 1, wherein the TRPA1 comprises the amino acid sequence of SEQ ID NO: 2, SEQ ID NO: 4 or SEQ ID NO: 6.

6. The screening method of claim 1, wherein the TRPA1 comprises an amino acid sequence having 95% or more sequence identity to the amino acid sequence of SEQ ID NO: 2.

7. The screening method of claim 1, wherein the TRPA1 comprises an amino acid sequence having 98% or more sequence identity to the amino acid sequence of SEQ ID NO: 2.

8. The screening method of claim 1, wherein the TRPA1 comprises an amino acid sequence having 99% or more sequence identity to the amino acid sequence of SEQ ID NO: 2.

9. The screening method of claim 1, comprising the following steps (a) to (c):
(a) a step for bringing a test substance into contact with mammalian cells that are expressing TRPA1;
(b) a step for analyzing the channel activity of TRPA1; and
(c) a step for selecting a substance capable of regulating the channel activity of TRPA1.

10. The screening method of claim 9, wherein the mammalian cells that are expressing TRPA1 are chromaffin cells, pancreatic β cells or cells transformed with a TRPA1 expression vector.

11. The screening method of claim 9, which is a method of screening for a prophylactic or therapeutic drug for constipation type irritable bowel syndrome, functional dyspepsia or constipation by selecting a substance capable of promoting the channel activity of TRPA1.

12. The screening method of claim 9, which is a method of screening for a prophylactic or therapeutic drug for diarrhea type irritable bowel syndrome, diarrhea or vomiting by selecting a substance capable of suppressing the channel activity of TRPA1.

* * * * *